(12) United States Patent
Keefe et al.

(10) Patent No.: US 11,273,149 B2
(45) Date of Patent: Mar. 15, 2022

(54) COMPOSITIONS AND METHODS FOR THE TREATMENT OF AMYOTROPHIC LATERAL SCLEROSIS, PARKINSON'S DISEASE, PARKINSON'S DISEASE WITH DEMENTIA, DEMENTIA WITH LEWY BODIES, AND MULTIPLE SYSTEM ATROPHY

(71) Applicants: Dennis Keefe, Bedford, MA (US); Guozhu Zheng, Lexington, MA (US)

(72) Inventors: Dennis Keefe, Bedford, MA (US); Guozhu Zheng, Lexington, MA (US); Vania Broccoli, Monza (IT)

(73) Assignee: STEALTH BIOTHERAPEUTICS INC., Needham, MA (US)

( * ) Notice: Subject to any disclaimer, the term of this patent is extended or adjusted under 35 U.S.C. 154(b) by 0 days.

(21) Appl. No.: 16/937,168

(22) Filed: Jul. 23, 2020

(65) Prior Publication Data
US 2021/0023062 A1     Jan. 28, 2021

Related U.S. Application Data

(60) Provisional application No. 62/878,272, filed on Jul. 24, 2019, provisional application No. 63/046,292, filed on Jun. 30, 2020.

(51) Int. Cl.

| | | |
|---|---|---|
| *A61K 31/4245* | (2006.01) |
| *A61P 25/28* | (2006.01) |
| *A61K 31/135* | (2006.01) |
| *A61K 31/197* | (2006.01) |
| *A61K 31/4152* | (2006.01) |
| *A61K 31/4178* | (2006.01) |
| *A61K 31/4184* | (2006.01) |
| *A61K 31/5513* | (2006.01) |
| *A61K 38/30* | (2006.01) |

(52) U.S. Cl.
CPC ........ *A61K 31/4245* (2013.01); *A61K 31/135* (2013.01); *A61K 31/197* (2013.01); *A61K 31/4152* (2013.01); *A61K 31/4178* (2013.01); *A61K 31/4184* (2013.01); *A61K 31/5513* (2013.01); *A61K 38/30* (2013.01); *A61P 25/28* (2018.01)

(58) Field of Classification Search
CPC .............. A61K 31/4245; A61K 31/135; A61K 31/197; A61K 31/4152; A61K 31/4178; A61K 31/4184; A61K 31/2213; A61K 38/30; A61P 25/28
See application file for complete search history.

(56) References Cited

U.S. PATENT DOCUMENTS

| 10,213,494 B2 * | 2/2019 | Schlossmacher ....... A61P 21/00 |
| 2013/0303346 A1 | 11/2013 | Barker |
| 2015/0239937 A1 | 8/2015 | Verdine et al. |
| 2017/0087204 A1 | 3/2017 | Wilson et al. |

FOREIGN PATENT DOCUMENTS

| WO | WO-2017/201433 | 11/2017 |
| WO | WO-2018/034901 | 2/2018 |
| WO | WO-2019/118878 | 6/2019 |

OTHER PUBLICATIONS

Valera et al. Neuropathol Appl Neurobiol. Feb. 2016 ; 42(1): 95-106.*
Wang et al. (Neuroscience Letters 636 (2017) 233-240).*
J. American Heart Association (2019, published first Jan. 13, 2019).*
Mayo Clinic 2020.*
NIH neurolological disorders Jan. & 2021.*
Del Signore, et al.,"Combined riluzole and sodium phenylbutyrate therapy in transgenic amyotrophic lateral sclerosis mice," Amyotrophic Lateral Schlerosis, vol. 10 (2009) (pp. 85-94).
Dossi, et al., "In Vivo Mitochondrial Function in Idiopathic and Genetic Parkinson's Disease," Metabolites, 2020, vol. 10, No. 19, pp. 1-11.
Filichia, et al. "Inhibition of Drp1 mitochondrial translocation provides neural protection in dopaminergic system in a Parkinson's disease model induced by MPTP." Scientific Reports, 2016, vol. 6, No. 32656, pp. 1-13.
Fowler, et al., "Longitudinal Quantification of Metabolites and Macromolecules Reveals Age- and Sex-Related Changes in the Healthy Fischer 344 Rat Brain."
Harris, et al., "High-field proton magnetic resonance spectroscopy reveals metabolic effects of normal brain aging," Neurobiology of Aging, Jul. 2014, vol. 35, No. 7, pp. 1686-1694.
International Search Report and Written Opinion on International Patent Application No. PCT/US2020/043287 dated Nov. 3, 2020 (580 pages).
Ito, et al. "Treatment with edaravone, initiated at symptom onset, slows motor decline and decreases SOD1 deposition in ALS mice," Experimental Neurology, 2008, vol. 213, pp. 448-455.
Joshi, et al. "Inhibitin of Drp1/Fis1 interaction slows progression or amyotropmc lateral sclerosis," EMBO Molecular Medicine, 2018, pp. 1-17.
Medinas, et al., "Proteostasis disturbance in amyotrophic lateral sclerosis," Human Molecular Genetics, vol. 26, No. R2 (2017) (pp. R91-R104).

(Continued)

*Primary Examiner* — Shirley V Gembeh
(74) *Attorney, Agent, or Firm* — Foley & Lardner LLP

(57) ABSTRACT

The present disclosure provides novel methods for treating or preventing amyotrophic lateral sclerosis (ALS), methods for delaying the onset of neurological symptoms associated with ALS, increasing survival in subjects afflicted with ALS, and attenuating the decline of muscle strength associated with ALS in a subject in need thereof. The present disclosure also provides methods for treating or preventing α-synucleinopathy or TDP-43 proteinopathy. The methods comprise administering to the subject an effective amount of a mitochondria-targeting peptidomimetic compound, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide, or a pharmaceutically acceptable salt, stereoisomer, tautomer, hydrate, and/or solvate thereof.

18 Claims, 10 Drawing Sheets

(56) References Cited

OTHER PUBLICATIONS

O'Connor, et al., "Plasma phospho-tau181 in presymptomatic and symptomatic familial Alzheimer's disease: a longitudinal cohort study," Molecular Psychiatry (2020).
Petri, et al., "Cell-permeable peptide antioxidants as a novel therapeutic approach in a mouse model of amyotrophic lateral sclerosis," Journal of Neurochemistry, 2006, vol. 98, No. 4, pp. 1141-1148.
Qi, et al. "A novel Drp1 inhibitor diminishes aberrant mitochondrial fission and neurotoxicity," Journal of Cell Science, 2012, vol. 126, pp. 789-802.
Rozas, et al., "The ER proteostasis network in ALS: Determining the differential motoneuron vulnerability," Neuroscience Letters vol. 636 (2017) (pp. 9-15).
Ryu, et al., "Sodium phenylbutyrate prolongs survival and regulates expression of anti-apoptotic genes in transgenic amyotrophic lateral sclerosis mice," Journal of Neurochemistry, vol. 93 (2005) (pp. 1087-1098).
Sreedharan, et al., "TDP-43 Mutations in Familial and Sporadic Amyotrophic Lateral Sclerosis," Science, Mar. 21, 2009, vol. 319, pp. 1668-1672.
Swerdlow, Russel H., "Mitochondria in Alzheimer brains," Neurology, Apr. 14, 2020, vol. 94, No. 15, pp. 646-647.
Szeto, Hazel H. "Development of Mitochondria-targeted Aromatic-cationic Peptides for Neurodegeneratie Diseases," Annals of the New York Academy of Sciences, vol. 1147, (2008) (pp. 112-121).
Tefera, et al. "Triheptanoin Protects Motor Neurons and Delays the Onset of Motor Symptoms in a Mouse Model of Amyotrophic Lateral Sclerosis," PLOS ONE, 2016, pp. 1-24.
Terada, et al. "In vivo mitochondrial and glycolytic impairments in patients with Alzheimer disease," Neurology, Apr. 14, 2020, vol. 94, No. 15, pp. e1592-e1604.
Thams, el al., "A Stem Cell-Based Screening Platform Identifies Compounds that Desensitize Motor Neurons to Endoplasmic Reticulum Stress," Molecular Therapy, vol. 27, No. 1 (2018) (pp. 1-15).
Vancova, et al., "In vivo and in vitro assessment of brain bioenergetics in aging rats," Journal of Cellular and Molecular Medicine, 2010, vol. 14, No. 11, pp. 2667-2674.
Yin, et al,. "Energy Metabolism and Inflammation in Brain Aging and Alzheimer's Disease," Free Radical Biology & Medicine, Nov. 2016, vol. 100, pp. 108-122.
Zhou, et al., "PD-linked CHCHD2 mutations impair CHCHD10 and MICOS complex leading to mitochondria dysfunction," Human Molecular Genetics vol. 28, No. 7 (2019) (pp. 1100-1116).
Annual Report Pursuant to Section 13 or 15(d) of the Securities Exchange Act (Stealth BioTherapeutics Corp Registration Statement).
SBT-272 for Rare Neurodegenerative Indications Slide (Nov. 2019).
Targeting the powerhouse of the cell to treat rare genetic and age-related diseases (Stealth Presentation) (Nov. 2019).
Written Opinion in International Patent Application No. PCT/US2018/065755 dated May 23, 2019 (6 pages).

* cited by examiner

Age, weeks

COMPOSITIONS AND METHODS FOR THE TREATMENT OF AMYOTROPHIC LATERAL SCLEROSIS, PARKINSON'S DISEASE, PARKINSON'S DISEASE WITH DEMENTIA, DEMENTIA WITH LEWY BODIES, AND MULTIPLE SYSTEM ATROPHY

CROSS-REFERENCE TO RELATED APPLICATIONS

The present application claims the benefit of priority to U.S. Application No. 62/878,272 filed on Jul. 24, 2019, and U.S. Application No. 63/046,292 filed on Jun. 30, 2020, the contents of which are incorporated herein in their entireties.

TECHNICAL FIELD

The present technology relates generally to compositions and methods for ameliorating or treating amyotrophic lateral sclerosis (ALS). The present technology also relates generally to compositions and methods for ameliorating or treating other neurodegenerative conditions such as α-synucleinopathies or TDP-43 proteinopathies, including Frontotemporal Lobar Degeneration (FTLD), Parkinson's disease (PD), PD with dementia, dementia with Lewy bodies, and Multiple System Atrophy. Additionally, the present technology relates to administering an effective amount of a mitochondria-targeting peptidomimetic compound, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide, or a pharmaceutically acceptable salt, stereoisomer, tautomer, hydrate, and/or solvate thereof, to a subject suffering from or at risk for ALS, α-synucleinopathies, or TDP-43 proteinopathies.

BACKGROUND

The following description is provided to assist the understanding of the reader. None of the information provided or references cited is admitted to be prior art to the compositions and methods disclosed herein.

Neurodegenerative disease and disorders affect a body's activities such as balance, movement, talking, breathing and/or heart function. Neurodegenerative disease and disorders are generally incurable and debilitating conditions that result in progressive degeneration and/or death of nerve cells. Some examples of neurodegenerative disease and disorders include: Amyotrophic lateral sclerosis (ALS), Frontotemporal Lobar Degeneration (FTLD), Parkinson's disease (PD), PD with dementia, dementia with Lewy bodies, and Multiple System Atrophy (MSA). Some neurodegenerative diseases can be characterized as an α-synucleinopathy or as a TDP-43 proteinopathy.

Amyotrophic lateral sclerosis (ALS) is a progressive neurodegenerative disorder that results in the death of motor neurons in the brain and spinal cord. The disorder generally strikes in mid-life, relentlessly leading to paralysis and death, typically three to five years after diagnosis. Up to 10% of ALS is familial, usually autosomal dominant. Several causative genes are known and, of these, mutant superoxide dismutase 1 (SOD1) and mutant C9orf72 (i.e., a $G_4C_2$ hexanucleotide repeat in the C9orf72 gene) are the most frequently found. Mutation of the TARDBP gene leading to modifications of the TAR DNA binding protein 43 (TDP-43) are also known to cause familial ALS (See Sreedharan et al., Science (2008), 319 (5870): 1668-1672). No effective treatments for ALS are available. Accordingly, there is a need in the art to develop treatment options for ALS.

SUMMARY

In one aspect, the present disclosure provides a method for treating or preventing amyotrophic lateral sclerosis (ALS) or Frontotemporal Lobar Degeneration (FTLD) in a subject in need thereof, comprising administering to the subject a therapeutically effective amount of a peptidomimetic such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide, or a pharmaceutically acceptable salt, stereoisomer, tautomer, hydrate, and/or solvate thereof.

In some embodiments, the subject has been diagnosed as having ALS or FTLD. In some embodiments, the ALS is familial. In some embodiments, the familial ALS is caused by a mutation in the superoxide dismutase 1 (SOD1) gene or mutation in the TARDBP gene leading to modification of the TAR DNA binding protein (TDP-43).

In some embodiments, the peptidomimetic is administered daily for 2 weeks or more. In some embodiments, the peptidomimetic is administered daily for 12 weeks or more.

In some embodiments, the treating or preventing comprises the treatment or prevention of one or more signs or symptoms of ALS or FTLD comprising one or more of muscle weakness, muscle wasting (atrophy), muscle fasciculations, muscle spasticity, slowness of movement, poor balance, incoordination, alterations in vocal quality, dysarthria, dysphagia, incomplete eye closure, drooling, pseudobulbar affect, premature death, and increased brain translocator protein-18 kDa (TSPO) expression. In some embodiments, the treating or preventing comprises the treatment or prevention of plasma accumulation of neurofilament light chain (NfL). In some embodiments, the treating or preventing comprises demonstrating improvement (e.g., increase) in neurite length in treated subjects as compared with subjects not treated with the peptidomimetic. In some embodiments, the treating or preventing comprises prolonging the lifespan in treated subjects as compared with subjects not treated with the peptidomimetic. In some embodiments, the treating or preventing comprises protection from axonal damage in the central nervous system (CNS). In some embodiments, the treating or preventing comprises delaying the progression of neurological symptom onset in treated subjects as compared with subjects not treated with the peptidomimetic.

In some embodiments, the subject is a mammal. In some embodiments, the mammalian subject is a human.

In some embodiments, the peptidomimetic is administered orally. In some embodiments, the peptidomimetic is administered subcutaneously. In some embodiments, the peptidomimetic is administered topically, intranasally, systemically, intravenously, intraperitoneally, intradermally, intraocularly, ophthalmically, intrathecally, intracerebroventricularly, iontophoretically, transmucosally, intravitreally, or intramuscularly.

In some embodiments, the method further comprises separately, sequentially, or simultaneously administering an additional treatment to the subject. In some embodiments, the additional treatment comprises administration of a therapeutic agent. In some embodiments, the therapeutic agent is selected from the group consisting of: riluzole (Rilutek®), edaravone (Radicava®), mecasermin, baclofen (Lioresal®), diazepam (Valium®), dantrolene (Dantrium®), nonsteroidal anti-inflammatory agents, anticonvulsive medications (e.g., carbamazepine (Tegretol) or phenytoin (Dilantin®)), amitriptyline (Elavil®), nortriptyline (Pamelor™), and Lorazepam (Ativan®). In some embodiments, the therapeutic agent is elamipretide (also known as SS-31 or bendavia). In some embodiments, the combination of peptidomimetic and an additional therapeutic treatment has a synergistic effect in the prevention or treatment of ALS or FTLD.

In some embodiments, the pharmaceutically acceptable salt of the peptidomimetic comprises a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt). In some embodiments, pharmaceutically acceptable salt comprises a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt, a mono-tosylate salt, a bis-tosylate salt, or a tri-tosylate salt. In some embodiments, the peptidomimetic is formulated as a tris-HCl salt, a bis-HCl salt, or a mono-HCl salt.

In one aspect, the present disclosure provides a use of a composition in the preparation of a medicament for treating or preventing amyotrophic lateral sclerosis (ALS) or Frontotemporal Lobar Degeneration (FTLD) in a subject in need thereof, wherein the composition comprises a therapeutically effective amount of a peptidomimetic such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide, or a pharmaceutically acceptable salt, stereoisomer, tautomer, hydrate, and/or solvate thereof.

In some embodiments, the subject has been diagnosed as having ALS or FTLD. In some embodiments, the ALS is familial. In some embodiments, the familial ALS is caused by a mutation in the superoxide dismutase 1 (SOD) gene or mutation in the TARDBP gene leading to modification of the TAR DNA binding protein (TDP-43).

In some embodiments, the peptidomimetic is intended to be administered daily for 2 weeks or more. In some embodiments, the peptidomimetic is intended to be administered daily for 12 weeks or more.

In some embodiments, the treating or preventing comprises the treatment or prevention of one or more signs or symptoms of ALS or FTLD comprising one or more of one or more of muscle weakness, muscle wasting (atrophy), muscle fasciculations, muscle spasticity, slowness of movement, poor balance, incoordination, alterations in vocal quality, dysarthria, dysphagia, incomplete eye closure, drooling, pseudobulbar affect, premature death, and increased brain translocator protein-18 kDa (TSPO) expression. In some embodiments, the treating or preventing comprises the treatment or prevention of plasma accumulation of neurofilament light chain (NfL). In some embodiments, the treating or preventing comprises demonstrating improvement (e.g., increase) in neurite length in treated subjects as compared with subjects not treated with the peptidomimetic. In some embodiments, the treating or preventing comprises prolonging the lifespan in treated subjects as compared with subjects not treated with the peptidomimetic. In some embodiments, the treating or preventing comprises protection from axonal damage in the central nervous system (CNS). In some embodiments, the treating or preventing comprises delaying the progression of neurological symptom onset in treated subjects as compared with subjects not treated with the peptidomimetic.

In some embodiments, the subject is a mammal. In some embodiments, the mammalian subject is a human.

In some embodiments, the peptidomimetic is formulated for administration orally. In some embodiments, the peptidomimetic is formulated for administration subcutaneously. In some embodiments, the peptidomimetic is formulated for administration, topically, intranasally, systemically, intravenously, intraperitoneally, intradermally, intraocularly, ophthalmically, intrathecally, intracerebroventricularly, iontophoretically, transmucosally, intravitreally, or intramuscularly.

In some embodiments, the peptidomimetic is intended to be separately, sequentially, or simultaneously used with an additional treatment. In some embodiments, the additional treatment comprises use of a therapeutic agent. In some embodiments, the therapeutic agent is selected from the group consisting of: riluzole (Rilutek®), edaravone (Radicava®), mecasermin, baclofen (Lioresal®), diazepam (Valium®), dantrolene (Dantrium®), nonsteroidal anti-inflammatory agents, anticonvulsive medications (e.g., carbamazepine (Tegretol) or phenytoin (Dilantin®)), amitriptyline (Elavil®), nortriptyline (Pamelor™), and Lorazepam (Ativan®). In some embodiments, the therapeutic agent is elamipretide (also known as SS-31 or bendavia). In some embodiments, the combination of peptidomimetic and an additional treatment has a synergistic effect in the prevention or treatment of ALS or FTLD.

In some embodiments, the pharmaceutically acceptable salt comprises a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt). In some embodiments, pharmaceutically acceptable salt comprises a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt, a mono-tosylate salt, a bis-tosylate salt, or a tri-tosylate salt. In some embodiments, the peptidomimetic is formulated as a tris-HCl salt, a bis-HCl salt, or a mono-HCl salt.

In one aspect, the present disclosure provides a peptidomimetic such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide, or a pharmaceutically acceptable salt, stereoisomer, tautomer, hydrate, and/or solvate thereof, for use in treating or preventing amyotrophic lateral sclerosis (ALS) or Frontotemporal Lobar Degeneration (FTLD) in a subject in need thereof.

In some embodiments, the subject has been diagnosed as having ALS or FTLD. In some embodiments, the ALS is familial. In some embodiments, the familial ALS is caused by a mutation in the superoxide dismutase 1 (SOD) gene or mutation in the TARDBP gene leading to modification of the TAR DNA binding protein (TDP-43).

In some embodiments, the peptidomimetic is intended to be administered daily for 2 weeks or more. In some embodiments, the peptidomimetic is intended to be administered daily for 12 weeks or more.

In some embodiments, the treating or preventing comprises the treatment or prevention of one or more signs or symptoms of ALS or FTLD comprising one or more of muscle weakness, muscle wasting (atrophy), muscle fasciculations, muscle spasticity, slowness of movement, poor balance, incoordination, alterations in vocal quality, dysarthria, dysphagia, incomplete eye closure, drooling, pseudobulbar affect, premature death, and increased brain translocator protein-18 kDa (TSPO) expression. In some embodiments, the treating or preventing comprises the treatment or prevention of plasma accumulation of neurofilament light chain (NfL). In some embodiments, the treating or preventing comprises demonstrating improvement (e.g. increase) in neurite length in treated subjects as compared with subjects not treated with the peptidomimetic. In some embodiments, the treating or preventing comprises prolonging the lifespan in treated subjects as compared with subjects not treated with the peptidomimetic. In some embodiments, the treating or preventing comprises protection from axonal damage in the central nervous system (CNS). In some embodiments, the treating or preventing comprises delaying the progression of neurological symptom onset in treated subjects as compared with subjects not treated with the peptidomimetic.

In some embodiments, the subject is a mammal. In some embodiments, the mammalian subject is a human.

In some embodiments, the peptidomimetic is formulated for administration orally. In some embodiments, the peptidomimetic is formulated for administration subcutaneously. In some embodiments, the peptidomimetic is formulated for administration topically, intranasally, systemically, intravenously, intraperitoneally, intradermally, intraocularly, ophthalmically, intrathecally, intracerebroventricularly, iontophoretically, transmucosally, intravitreally, or intramuscularly.

In some embodiments, the peptidomimetic is intended to be separately, sequentially, or simultaneously used with an additional treatment. In some embodiments, the additional treatment comprises use of a therapeutic agent. In some embodiments, the therapeutic agent is selected from the group consisting of: riluzole (Rilutek®), edaravone (Radicava®), mecasermin, baclofen (Lioresal®), diazepam (Valium®), dantrolene (Dantrium®), nonsteroidal anti-inflammatory agents, anticonvulsive medications (e.g., carbamazepine (Tegretol) or phenytoin (Dilantin®)), amitriptyline (Elavil®), nortriptyline (Pamelor™), and Lorazepam (Ativan®). In some embodiments, the therapeutic agent is elamipretide (also known as SS-31 or bendavia). In some embodiments, the combination of peptidomimetic and an additional treatment has a synergistic effect in the prevention or treatment of ALS or FTLD.

In some embodiments, the pharmaceutically acceptable salt comprises a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt). In some embodiments, pharmaceutically acceptable salt comprises a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt, a mono-tosylate salt, a bis-tosylate salt, or a tri-tosylate salt. In some embodiments, the peptidomimetic is formulated as a tris-HCl salt, a bis-HCl salt, or a mono-HCl salt.

In one aspect, the present disclosure provides a method for treating or preventing α-synucleinopathy or TDP-43 proteinopathy in a subject in need thereof, comprising administering to the subject a therapeutically effective amount of a peptidomimetic such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide, or a pharmaceutically acceptable salt, stereoisomer, tautomer, hydrate, and/or solvate thereof. In some embodiments, the subject has been diagnosed as having an α-synucleinopathy or a TDP-43 proteinopathy.

In some embodiments, the α-synucleinopathy is Parkinson's Disease (PD), PD with dementia, dementia with Lewy bodies, or Multiple System Atrophy, and the TDP-43 proteinopathy is amyotrophic lateral sclerosis (ALS) or Frontotemporal Lobar Degeneration (FTLD).

In some embodiments, the peptidomimetic is administered daily for 2 weeks or more. In some embodiments, the peptidomimetic is administered daily for 12 weeks or more.

In some embodiments, the treating or preventing of α-synucleinopathy comprises attenuating the loss of dopaminergic neurons in the subject as compared to untreated controls. In some embodiments, the treating or preventing of TDP-43 proteinopathy comprises an improvement (e.g., increase) in neurite length in the subject as compared to untreated controls.

In some embodiments, the subject is a mammal. In some embodiments, the mammalian subject is a human.

In some embodiments, the peptidomimetic is administered orally. In some embodiments, the peptidomimetic is administered subcutaneously. In some embodiments, the peptidomimetic is administered topically, intranasally, systemically, intravenously, intraperitoneally, intradermally, intraocularly, ophthalmically, intrathecally, intracerebroventricularly, iontophoretically, transmucosally, intravitreally, or intramuscularly.

In some embodiments, the method further comprises separately, sequentially, or simultaneously administering an additional treatment to the subject. In some embodiments, the additional treatment comprises administration of a therapeutic agent. In some embodiments, the therapeutic agent comprises levodopa for the treatment of α-synucleinopathy, and the therapeutic agent comprises a selective serotonin reuptake inhibitor (SSRI) antidepressant for the treatment of TDP-43 proteinopathy. In some embodiments, the combination of peptidomimetic and an additional therapeutic treatment has a synergistic effect in the prevention or treatment of α-synucleinopathy or TDP-43 proteinopathy.

In some embodiments, the pharmaceutically acceptable salt comprises a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt). In some embodiments, pharmaceutically acceptable salt comprises a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt, a mono-tosylate salt, a bis-tosylate salt, or a tri-tosylate salt. In some embodiments, the peptidomimetic is formulated as a tris-HCl salt, a bis-HCl salt, or a mono-HCl salt.

In one aspect, the present disclosure provides a use of a composition in the preparation of a medicament for treating or preventing α-synucleinopathy or TDP-43 proteinopathy in a subject in need thereof, wherein the composition comprises a therapeutically effective amount of the peptidomimetic such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide, or a pharmaceutically acceptable salt, stereoisomer, tautomer, hydrate, and/or solvate thereof.

In some embodiments, the subject has been diagnosed as having an α-synucleinopathy or a TDP-43 proteinopathy. In some embodiments, the α-synucleinopathy is Parkinson's Disease (PD), PD with dementia, dementia with Lewy bodies, or Multiple System Atrophy, and the TDP-43 proteinopathy is amyotrophic lateral sclerosis (ALS) or Frontotemporal Lobar Degeneration (FTLD).

In some embodiments, the peptidomimetic is intended to be administered daily for 2 weeks or more. In some embodiments, the peptidomimetic is intended to be administered daily for 12 weeks or more.

In some embodiments, the treating or preventing of α-synucleinopathy comprises attenuating the loss of dopaminergic neurons in the subject as compared to untreated controls. In some embodiments, the treating or preventing of TDP-43 proteinopathy comprises an improvement (e.g., increase) in neurite length in the subject as compared to untreated controls.

In some embodiments, the subject is a mammal. In some embodiments, the mammalian subject is a human.

In some embodiments, the peptidomimetic is formulated for administration orally. In some embodiments, the peptidomimetic is formulated for administration subcutaneously. In some embodiments, the peptidomimetic is formulated for administration, topically, intranasally, systemically, intravenously, intraperitoneally, intradermally, intraocularly, ophthalmically, intrathecally, intracerebroventricularly, iontophoretically, transmucosally, intravitreally, or intramuscularly.

In some embodiments, the use further comprises separately, sequentially, or simultaneously administering an additional treatment to the subject. In some embodiments, the additional treatment comprises administration of a therapeutic agent. In some embodiments, the therapeutic agent comprises levodopa for the treatment of α-synucleinopathy, and the therapeutic agent comprises a selective serotonin reuptake inhibitor (SSRI) antidepressant for the treatment of TDP-43 proteinopathy.

In some embodiments, the combination of peptidomimetic and an additional therapeutic treatment has a synergistic effect in the prevention or treatment of α-synucleinopathy or TDP-43 proteinopathy.

In some embodiments, the pharmaceutically acceptable salt comprises a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt). In some embodiments, pharmaceutically acceptable salt comprises a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt, a mono-tosylate salt, a bis-tosylate salt, or a tri-tosylate salt. In some embodiments, the peptidomimetic is formulated as a tris-HCl salt, a bis-HCl salt, or a mono-HCl salt.

In one aspect, the present disclosure provides a peptidomimetic such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide, or a pharmaceutically acceptable salt, stereoisomer, tautomer, hydrate, and/or solvate thereof, for use in treating or preventing α-synucleinopathy or TDP-43 proteinopathy in a subject in need thereof.

In some embodiments, the subject has been diagnosed as having an α-synucleinopathy or a TDP-43 proteinopathy. In some embodiments, the α-synucleinopathy is Parkinson's Disease (PD), PD with dementia, dementia with Lewy bodies, or Multiple System Atrophy, and the TDP-43 proteinopathy is amyotrophic lateral sclerosis (ALS) or Frontotemporal Lobar Degeneration (FTLD).

In some embodiments, the peptidomimetic is intended to be administered daily for 2 weeks or more. In some embodiments, the peptidomimetic is intended to be administered daily for 12 weeks or more.

In some embodiments, the treating or preventing of α-synucleinopathy comprises attenuating the loss of dopaminergic neurons in the subject as compared to untreated controls. In some embodiments, the treating or preventing of TDP-43 proteinopathy comprises an improvement (e.g., increase) in neurite length in the subject as compared to untreated controls.

In some embodiments, the subject is a mammal. In some embodiments, the mammalian subject is a human.

In some embodiments, the peptidomimetic is formulated for administration orally. In some embodiments, the peptidomimetic is formulated for administration subcutaneously. In some embodiments, the peptidomimetic is formulated for administration topically, intranasally, systemically, intravenously, intraperitoneally, intradermally, intraocularly, ophthalmically, intrathecally, intracerebroventricularly, iontophoretically, transmucosally, intravitreally, or intramuscularly.

In some embodiments, the peptidomimetic is intended to be separately, sequentially, or simultaneously used with an additional treatment. In some embodiments, the additional treatment comprises use of a therapeutic agent. In some embodiments, the therapeutic agent comprises levodopa for the treatment of α-synucleinopathy, and the therapeutic agent comprises a selective serotonin reuptake inhibitor (SSRI) antidepressant for the treatment of TDP-43 proteinopathy. In some embodiments, the combination of peptidomimetic and an additional therapeutic treatment has a synergistic effect in the prevention or treatment of α-synucleinopathy or TDP-43 proteinopathy.

In some embodiments, the pharmaceutically acceptable salt comprises a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt). In some embodiments, pharmaceutically acceptable salt comprises a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt, a mono-tosylate salt, a bis-tosylate salt, or a tri-tosylate salt. In some embodiments, the peptidomimetic is formulated as a tris-HCl salt, a bis-HCl salt, or a mono-HCl salt.

BRIEF DESCRIPTION OF THE DRAWINGS

FIGS. 1A and 1B are charts showing the progression of neurological symptom onset in male and female SOD1 G93A mice treated with (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide-3HCl (Ia) at doses of 0.5 mg/kg or 5.0 mg/kg relative to vehicle treated controls.

FIGS. 1C and 1D are Kaplan-Meier survival curves depicting the lifespan of male and female SOD1 G93A mice treated with 0.5 mg/kg or 5.0 mg/kg (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide.3HCl (Ia) relative to vehicle treated controls. *(Ia) @ 5.0 mg/kg, p<0.05.

FIGS. 2A and 2B are charts showing the grip strength determined at baseline (week 8) and through end of life for each animal receiving 0.5 mg/kg or 5.0 mg/kg (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (Formula I) relative to vehicle treated controls.

FIGS. 3A and 3B are charts depicting plasma levels of NfL following 10 weeks of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide or vehicle control administration in male and female SOD1 G93A mice.

DETAILED DESCRIPTION

Figure 1A:
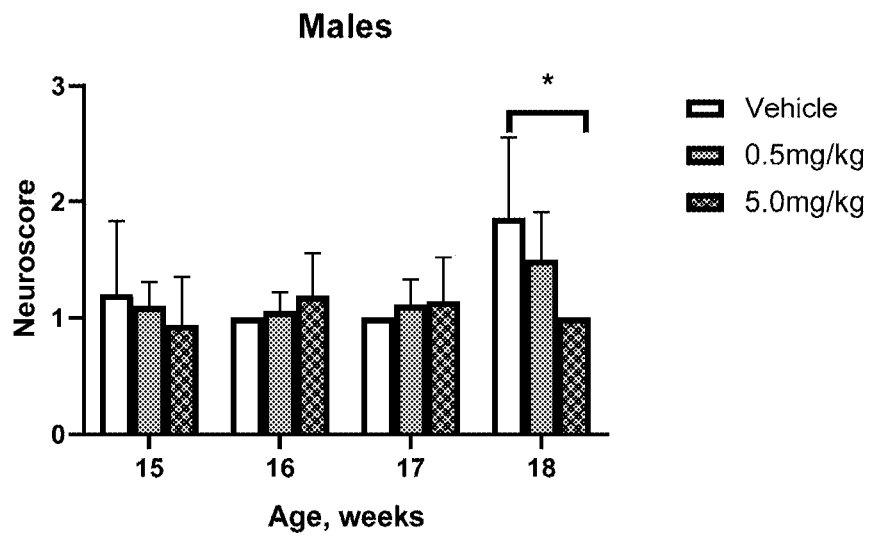
FIGS. 1A-1D: Systemic administration of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide, or a pharmaceutically acceptable salt, stereoisomer, tautomer, hydrate, and/or solvate thereof, delays neurological disease symptom onset and prolongs lifespan in male SOD1 G93A transgenic mice.

It is to be appreciated that certain aspects, modes, embodiments, variations and features of the present technology are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this present technology belongs.

In practicing the present technology, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); Nucleic Acid Hybridization, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, Meth. Enzymol., (Academic Press, Inc., 1984); *Gene Transfer Vectors for Mammalian Cells*, Miller & Calos, Eds. (Cold Spring Harbor Laboratory, N Y, 1987); and *Meth. Enzymol.*, Vols. 154 and 155, Wu & Grossman, and Wu, Eds., respectively.

Definitions

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, therapeutic agent, peptide or peptidomimetic to a subject includes any route of introducing or delivering to a subject a compound to perform its intended function. Administration can be carried out by any suitable route, such as oral administration. Administration can be carried out subcutaneously. Administration can be carried out intravenously. Administration can be carried out intraocularly. Administration can be carried out systemically. Alternatively, administration may be carried out topically, intranasally, intraperitoneally, intradermally, ophthalmically, intrathecally, intracerebroventricularly, iontophoretically, transmucosally, intravitreally, or intramuscularly. Administration includes self-administration and the administration by another.

As used herein, the term "amino acid" includes both a naturally occurring amino acid and a non-natural amino acid. The term "amino acid," unless otherwise indicated, includes both isolated amino acid molecules (i.e., molecules that include both, an amino-attached hydrogen and a carbonyl carbon-attached hydroxyl) and residues of amino acids (i.e., molecules in which either one or both an amino-attached hydrogen or a carbonyl carbon-attached hydroxyl are removed). The amino group can be alpha-amino group, beta-amino group, etc. For example, the term "amino acid alanine" can refer either to an isolated alanine H-Ala-OH or to any one of the alanine residues H-Ala-, -Ala-OH, or -Ala-. Unless otherwise indicated, all amino acids found in the compounds described herein can be either in D or L configuration. An amino acid that is in D configuration may be written such that "D" precedes the amino acid abbreviation. For example, "D-Arg" represents arginine in the D configuration. The term "amino acid" includes salts thereof, including pharmaceutically acceptable salts. Any amino acid can be protected or unprotected. Protecting groups can be attached to an amino group (for example alpha-amino group), the backbone carboxyl group, or any functionality of the side chain. As an example, phenylalanine protected by a benzyloxycarbonyl group (Z) on the alpha-amino group would be represented as Z-Phe-OH.

With the exception of the N-terminal amino acid, all abbreviations of amino acids (for example, Phe) in this disclosure stand for the structure of NH—C(R)(R')—CO—, wherein R and R' each is, independently, hydrogen or the side chain of an amino acid (e.g., R=benzyl and R'=H for Phe). Accordingly, phenylalanine is H-Phe-OH. The designation "OH" for these amino acids, or for peptides (e.g., Lys-Val-Leu-OH) indicates that the C-terminus is the free acid. The designation "NH$_2$" in, for example, Phe-D-Arg-Phe-Lys-NH$_2$ indicates that the C-terminus of the protected peptide fragment is amidated. Further, certain R and R', separately, or in combination as a ring structure, can include functional groups that require protection during the liquid phase or solid phase synthesis.

Where the amino acid has isomeric forms, it is the L form of the amino acid that is represented unless otherwise explicitly indicated as D form, for example, D-Arg. Notably, many amino acid residues are commercially available in both D- and L-form. For example, D-Arg is a commercially available D-amino acid.

A capital letter "D" used in conjunction with an abbreviation for an amino acid residue refers to the D-form of the amino acid residue.

The term "DMT" refers to 2,6-di(methyl)tyrosine (e.g., 2,6-dimethyl-L-tyrosine; CAS 123715-02-6).

As used herein, the phrase "delaying the onset of" refers to, in a statistical sample, postponing, hindering, or causing one or more symptoms of a disorder, symptom, condition or indication to occur more slowly than normal in a treated sample relative to an untreated control sample.

As used herein, the term "effective amount" refers to a quantity sufficient to achieve a desired therapeutic and/or prophylactic effect, e.g., an amount which results in partial or full amelioration of one or more symptoms of ALS, α-synucleinopathies, or TDP-43 proteinopathies. In the context of therapeutic or prophylactic applications, in some embodiments, the amount of a composition administered to the subject will depend on the type, degree, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, mitochondria-targeting peptidomimetics, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (e.g., (Ia), such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt (i.e. a salt comprising one acetate moiety), a bis-acetate salt (i.e., a salt comprising two acetate moieties), a tri-acetate salt, (i.e., a salt comprising three acetate moieties), a mono-trifluoroacetate salt (i.e., a salt comprising one trifluoroacetate moiety), a bis-trifluoroacetate salt (i.e. a salt comprising two trifluoroacetate moieties), a tri-trifluoroacetate salt (i.e., a salt comprising three trifluoroacetate moieties), a monohydrochloride salt (i.e., a salt comprising one chloride anion such as resulting from or as would be regarded as resulting from inclusion of HCl; a "mono-HCl salt"), a bis-hydrochloride salt (i.e., a salt comprising two chloride anions such as resulting from or as would be regarded as resulting from inclusion of two HCl; a "bis-HCl salt"), a trihydrochloride salt (i.e., a salt comprising three chloride anions such as resulting from or as would be regarded as resulting from inclusion of three HCl; a "tri-HCl salt"), a mono-tosylate salt (i.e., a salt comprising one tosylate moiety), a bis-tosylate salt (i.e., a salt comprising two tosylate moieties), or a tri-tosylate salt (i.e., a salt comprising three tosylate moieties), may be administered to a subject having one or more signs, symptoms, or risk factors of ALS or FTLD, including, but not limited to, muscle weakness, muscle wasting (atrophy), muscle fasciculations, muscle spasticity, slowness of movement, poor balance, incoordination, alterations in vocal quality, dysarthria, dysphagia, incomplete eye closure, drooling, pseudobulbar affect, premature death, increased brain translocator protein-18 kDa (TSPO) expression, and plasma accumulation of neurofilament light chain (NfL).

As used herein, the term "hydrate" refers to a compound which is associated with water. The number of the water molecules contained in a hydrate of a compound may be (or may not be) in a definite ratio to the number of the compound molecules in the hydrate.

As used herein, the terms "peptidomimetic" refers to a small peptide-like polymer comprising two or more amino acids but that also contains a non-peptide-like modification. A peptidomimetic can arise either by modification of an existing peptide, or by designing similar molecules that mimic peptide function.

The terms "pharmaceutically acceptable carrier" and "carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in *Remington's Pharmaceutical Sciences* by E.W. Martin, herein incorporated by reference in its entirety.

As used herein, "prevention" or "preventing" of a disorder or condition refers to a compound that, in a statistical sample, reduces the occurrence of the disorder or condition in the treated sample relative to an untreated control sample, or delays the onset of one or more symptoms of the disorder or condition relative to the untreated control sample. As used herein, preventing ALS, α-synucleinopathies, or TDP-43 proteinopathies, includes preventing or delaying the initiation of symptoms of ALS, α-synucleinopathies, or TDP-43 proteinopathies. As used herein, prevention of ALS, α-synucleinopathies, or TDP-43 proteinopathies also includes preventing a recurrence of one or more signs or symptoms of ALS, α-synucleinopathies, or TDP-43 proteinopathies.

As used herein, the terms "subject" and "patient" are used interchangeably.

In the context of therapeutic use or administration, the term "separate" or "separately" refers to an administration of at least two active ingredients by different routes, formulations, and/or pharmaceutical compositions.

The term "simultaneous" therapeutic use refers to administration of at least two active ingredients at the same time or at substantially the same time. In some embodiments, simultaneous administration includes but is not limited to administration of a single composition or formulation comprising at least two active ingredients, co-administration of at least two separate active ingredients by the same route, and co-administration of at least two separate active ingredients by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "subject" refers to a living animal. In various embodiments, a subject is a mammal. In some embodiments, a subject is a non-human mammal, including, without limitation, a mouse, rat, hamster, guinea pig, rabbit, sheep, goat, cat, dog, pig, minipig, horse, cow, or non-human primate. In some embodiments, the subject is a human.

As used herein, the term "solvate" refers to forms of a compound (e.g. peptide or peptidomimetic) that are associated with a solvent, usually by a solvolysis reaction. This physical association may include hydrogen bonding. Conventional solvents include water, methanol, ethanol, isopropanol, acetic acid, ethyl acetate, acetone, hexane(s), dimethyl sulfoxide (DMSO), tetrahydrofuran (THF), diethyl ether, and the like As used herein, the term "tautomer" refers to compounds that are interchangeable forms of a particular compound structure, and that vary in the displacement of hydrogen atoms and electrons. Thus, two structures may be in equilibrium through the movement of 7 electrons and an atom (usually H). For example, enols and ketones are tautomers because they are rapidly interconverted by treatment with either acid or base. Tautomeric forms may be relevant to the attainment of the optimal chemical reactivity and biological activity of a compound of interest As used herein, a "synergistic therapeutic effect" refers to a greater-than-additive therapeutic effect which is produced by a combination of at least two agents, and which exceeds that which would otherwise result from the individual administration of the agents. For example, lower doses of one or more agents may be used in treating ALS, α-synucleinopathies, or TDP-43 proteinopathies, resulting in increased therapeutic efficacy and decreased side-effects.

As used herein, the terms "treating" or "treatment" or "alleviation" refers to therapeutic treatment, wherein the object is to reduce, alleviate or slow down the progression or advancement of, and/or reverse the progression of the targeted pathological condition or disorder. A subject is successfully "treated" for ALS, α-synucleinopathies, or TDP-43 proteinopathies if, after receiving a therapeutic amount of a mitochondria-targeting peptidomimetic, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (e.g., (Ia)), such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a tri-hydrochloride salt, a mono-tosylate salt, a bis-tosylate salt, or a tri-tosylate salt, according to the methods described herein, the subject shows observable and/or measurable reduction in or absence of one or more signs and symptoms of ALS, α-synucleinopathies, or TDP-43 proteinopathies. For example, in ALS, such signs and symptoms include, but are not limited to, muscle weakness, muscle wasting (atrophy), muscle fasciculations, muscle spasticity, slowness of movement, poor balance, incoordination, alterations in vocal quality, dysarthria, dysphagia, incomplete eye closure, drooling, pseudobulbar affect, premature death, increased brain translocator protein-18 kDa (TSPO) expression, and plasma accumulation of neurofilament light chain (NfL). In some embodiments, treatment refers to a delay in the onset of neurological symptoms of ALS as assessed by neurological scoring as described herein.

It is also to be appreciated that the various modes of treatment or prevention of medical conditions as described herein are intended to mean "substantial," which includes total but also less than total treatment or prevention, and wherein some biologically or medically relevant result is achieved.

As used herein, the terms "(R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide," "(D-Arg-DMT-NH((S)-5-amino-1-(3-benzyl-1,2,4-oxadiazol-5-yl)pent-1-yl),", (2R)-2-amino-N-[(1S)-1-{[(1S)-5-amino-1-(3-benzyl-1,2,4-oxadiazol-5-yl)pentyl]carbamoyl}-2-(4-hydroxy-2,6-dimethylphenyl)ethyl]-5-carbamimidamidopentanamide, "compound 7a," and "7a" refer to the same mitochondria-targeting peptidomimetic, are used interchangeably herein, and refer to a compound of the following formula (I):

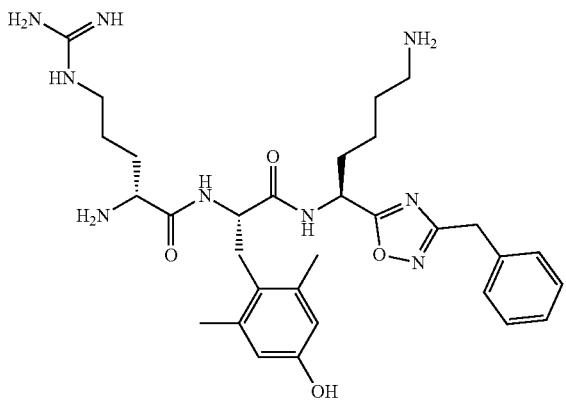

(R)-2-amino-N—((S)-1-(((S)-5-amino-1-(3-benzyl-
1,2,4-oxadiazol-5-yl)pentyl)amino)-3-(4-hydroxy-2,
6-dimethylphenyl)-1-oxopropan-2-yl)-5-guanidino-
pentanamide The term "(R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide,", (2R)-2-amino-N-[(1S)-1-{[(1S)-5-amino-1-(3-benzyl-1,2,4-oxadiazol-5-yl)pentyl]carbamoyl}-2-(4-hydroxy-2,6-dimethylphenyl)ethyl]-5-carbamimidamidopentanamide, "(D-Arg-DMT-NH((S)-5-amino-1-(3-benzyl-1,2,4-oxadiazol-5-yl)pent-1-yl)," "compound 7a," and "7a (as illustrated below)" is intended to include pharmaceutically acceptable salt forms thereof such as the tri- (or tris)-HCl salt of formula (Ia):

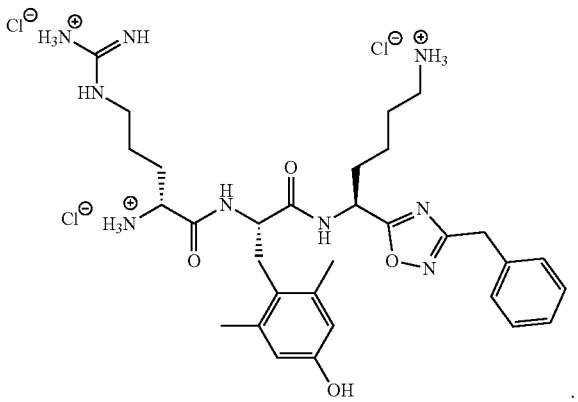

Amyotrophic Lateral Sclerosis (ALS)

Amyotrophic lateral sclerosis (ALS; also known as Lou Gehrig's disease) is a progressive neuromuscular condition characterized by weakness, muscle wasting, fasciculations, and increased reflexes. Approximately 30,000 Americans are currently afflicted with the disease. The annual incidence rate is one to two cases per 100,000. The disease is most commonly diagnosed in middle age and affects more men than women. ALS is characterized by adult-onset, idiopathic, progressive degeneration of anterior horn cells and upper and lower motor neurons resulting in progressive muscle weakness, wasting, and fasciculations. Atrophy of the anterior horn cells and replacement of the large motor neurons by fibrous astrocytes (gliosis) causes the affected anterior and lateral columns of the spinal cord to become hard, hence the term "lateral sclerosis." Typical signs and symptoms of ALS include muscle weakness, muscle wasting (atrophy), muscle fasciculations, muscle spasticity, slowness of movement, poor balance, incoordination, alterations in vocal quality, dysarthria, dysphagia, incomplete eye closure, drooling, pseudobulbar affect, and premature death.

Up to 10% of ALS is familial, usually autosomal dominant. Several causative genes are known and, of these, mutant superoxide dismutase 1 (SOD) and mutant C9orf72 (i.e., a $G_4C_2$ hexanucleotide repeat in the C9orf72 gene) are the most frequently found among familial ALS (fALS) and sporadic ALS (sALS). Several other genes are known to be causative of classical ALS, although these account for a lower percentage of cases than does mutant SOD1; these genes include mutant FUS (fused in sarcoma), mutant TAR-DBP gene leading to modifications of the TAR DNA binding protein 43 (TDP-43), and optineurin.

The clinical presentation varies, depending on the area of the nervous system that is damaged and progression of the pathologic changes. The classic presentation of ALS is insidious, progressive, asymmetric muscular weakness and atrophy along with neurologic signs, particularly fasciculations and hyperreflexia. It usually presents with problems in dexterity or gait resulting from muscle weakness. Difficulty in speaking or swallowing is the initial symptom in the bulbar form of the disease. Over a period of months or years, patients with ALS develop severe, progressive muscular weakness and other symptoms caused by loss of function in both upper and lower motor neurons. Sphincter control, sensory function, intellectual abilities and skin integrity are preserved. Patients become completely disabled, often requiring ventilatory support and gastrostomy. Death usually occurs within five years of diagnosis and is attributed to respiratory failure or cachexia. The diagnosis of ALS is clinical, based on the characteristic signs of progressive weakness, atrophy, fasciculations and hyperreflexia affecting several regions of the body. The early differential diagnosis may include musculoskeletal, neurologic or systemic conditions. The etiology of the disease is unknown. Current management involves aggressive, individualized alleviation of symptoms and complications. There is no cure for ALS.

The only agents currently labeled for the treatment of ALS are riluzole (Rilutek®) and edaravone (Radicava®). At least one other drug (mecasermin) is under consideration by the U.S. Food and Drug Administration. Various symptomatic treatments including baclofen (Lioresal®), diazepam (Valium®), dantrolene (Dantrium®), nonsteroidal anti-inflammatory agents, anticonvulsive medications, such as carbamazepine (Tegretol) or phenytoin (Dilantin®), amitriptyline (Elavil®), nortriptyline (Pamelor™), or Lorazepam (Ativan®), may be helpful.

Neurofilament Light Chain (NfL) Biomarkers, which reflect hallmarks of ALS, may not only aid in the diagnostic algorithm of the disease, but could also be of value in defining homogeneous subgroups of patients. They can also be helpful to track disease progression and treatment responses.

Neurofilaments (NF) have been studied extensively in different neurological conditions and are considered to be useful as marker of acute and chronic neuronal injury (Bacioglu et al., Neuron 91:56-66 (2016)). Neurofilaments are intermediate filaments of 10 nm in neurons, composed of heteropolymers of different subunits, neurofilament light chain (NfL), neurofilament medium chain (NfM), and neurofilament heavy chain (NfH) (Lee, *Ann. Rev. Neurosci.* 19:187-217 (1996)). Neurofilament light chains (NfL) are unique to neuronal cells, are shed to the cerebrospinal fluid (CSF), and are detectable at low concentrations in peripheral blood. CSF, serum, and plasma NfL levels have been shown to discriminate patients with ALS from healthy controls with high sensitivity and specificity, and correlate with disease progression or survival in patients with ALS (Lu et al., *Neurology* 2015 Jun. 2; 84(22):2247-57). In the SOD1 mouse model of ALS, the degeneration of motor neurons has been shown to be accompanied by a progressive rise in blood NF levels, and these levels have been shown to be able to capture treatment responses (Lu et al., *PLoS ONE* 7:e40998 (2012); Boylan et al., *J. Neurochem.* 111:1182-1191 (2009)).

α-Synucleinopathies

Synucleinopathies or α-synucleinopathies are neurodegenerative diseases characterized by the abnormal accumulation of aggregates of α-synuclein protein in neurons, nerve fibers, or glial cells. These conditions are also associated with the loss of substantia nigra dopaminergic neurons. These diseases include Parkinson's Disease (PD). PD with dementia, dementia with Lewy bodies, and Multiple System Atrophy. The neuropathologic diagnosis of a α-synucleinopathy is based on detection of altered α-synuclein in the tissue and registration of the neuroanatomic distribution of this alteration in the brain.

TDP-43 Proteinopathies

TAR-DNA binding protein 43 (TDP-43) proteinopathies include ALS and frontotemporal lobar degeneration (FTLD). FTLD refers to a clinically, genetically, and neuropathologically heterogeneous group of neurodegenerative disorders and is the third most common form of dementia after Alzheimer disease (AD) and dementia with Lewy bodies. Current research criteria divide FTLD into the following 3 clinical syndromes: frontotemporal dementia, primary progressive nonfluent aphasia, and semantic dementia. Frontotemporal dementia, the most common clinical form, primarily manifests as personality and behavioral changes, while primary progressive nonfluent aphasia and semantic dementia manifest predominantly as language dysfunctions. In addition, patients may develop movement abnormalities such as parkinsonism and motor neuron disease.

The term frontotemporal lobar degeneration reflects the prominent frontal and temporal lobe atrophy seen in these patients by neuropathological examination. A characteristic feature in most FTLD brains is the formation of abnormal protein inclusions in neurons and glial cells. TAR-DNA binding protein 43 (TDP-43) has been identified as the disease protein in FTLD. Mutant TDP-43 has been found to inhibit neurite outgrowth, and over-expression of wild-type (WT) and mutant TDP43 causes toxicity in motor neurons.

Mitochondria-Targeting Peptidomimetics

In some embodiments, the present disclosure provides a compound of formula (II), or a pharmaceutically acceptable salt, stereoisomer, tautomer, hydrate, and/or solvate thereof:

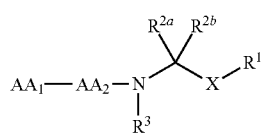

(II)

wherein $AA_1$ is selected from

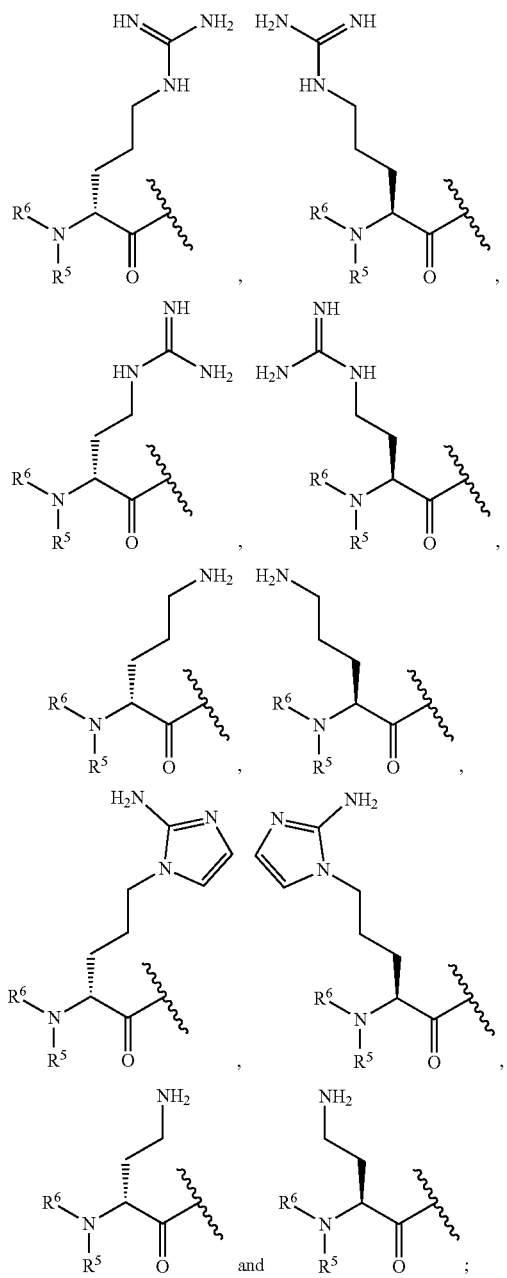

$AA_2$ is selected from

-continued

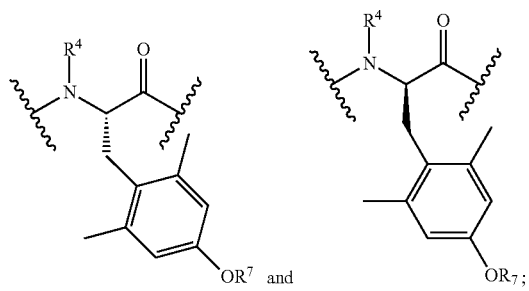

R¹ is selected from

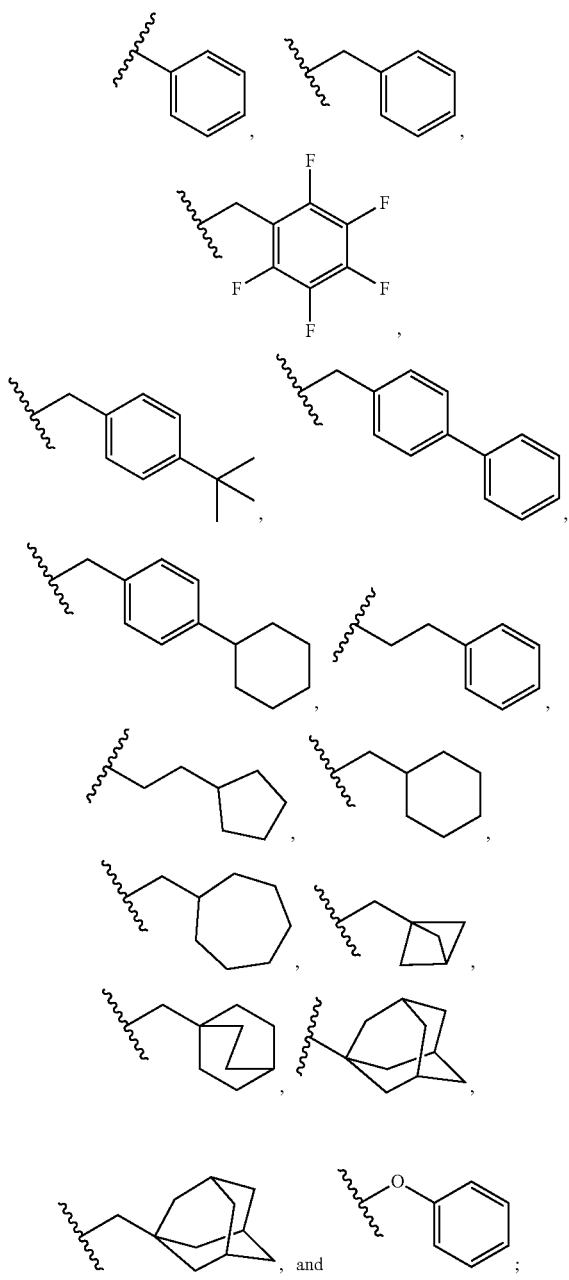

R²ᵃ is selected from

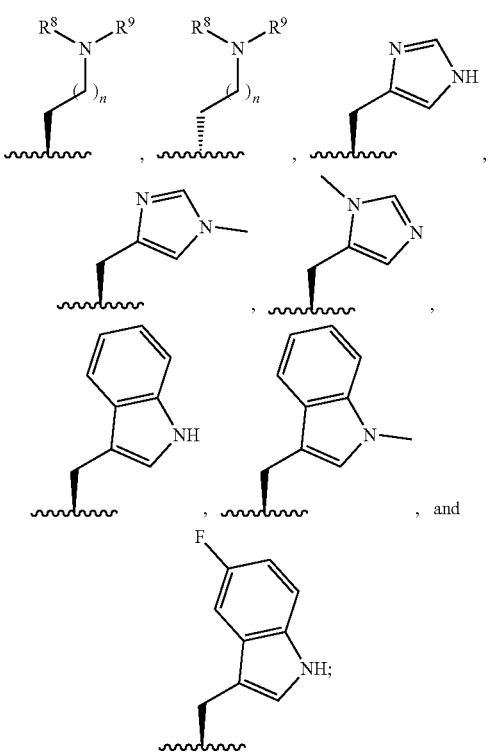

R²ᵇ is H or Me;

R³ and R⁴ are independently selected from H and (C₁-C₆)alkyl;

R⁵ and R⁶ are independently H, methyl, ethyl, propyl, cyclopropyl, or cyclobutyl; or R⁵ and R⁶ together with the N atom to which they are attached form a 4-6-membered heterocyclyl;

R⁷ is selected from H, (C₁-C₆)alkyl, cycloalkyl, and aryl;

R⁸ and R⁹ are independently selected from H, (C₁-C₆) alkyl, cycloalkyl, and aryl; or R⁸ and R⁹ together with the N atom to which they are attached form a 4-6-membered heterocyclyl;

n is 1, 2, or 3;

X is selected from

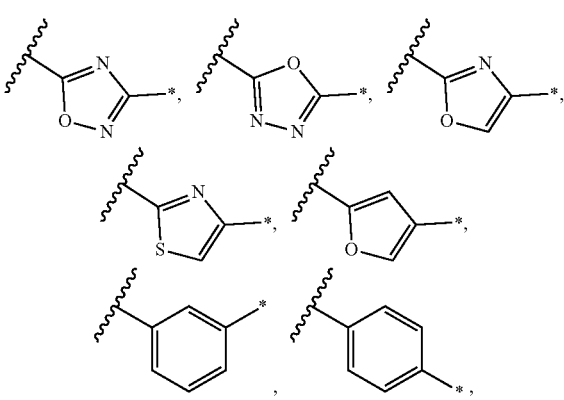

-continued
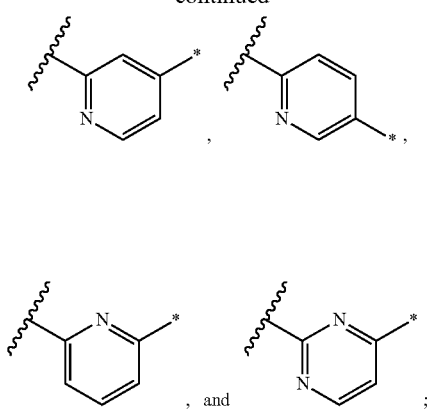
, and ;
and
* denotes the point of attachment of X to $R^1$.
In some embodiments, $AA_1$ is
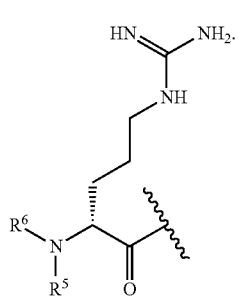
In some embodiments, $AA_1$ is
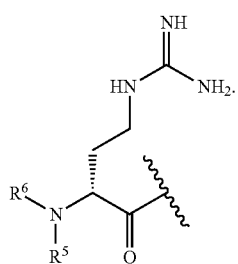
In some embodiments, $AA_1$ is
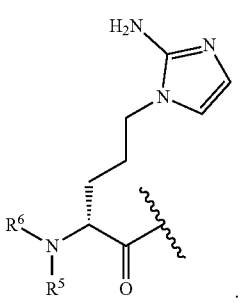
In some embodiments, $AA_1$ is
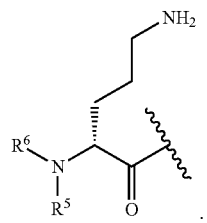
In some embodiments, $AA_1$ is
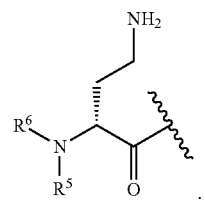
In some embodiments, $AA_2$ is
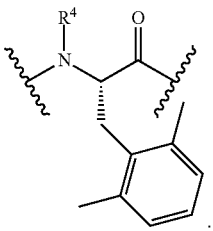
In some embodiments, $AA_2$ is
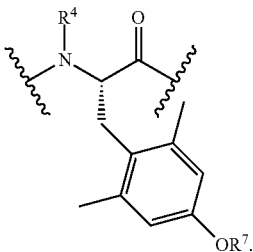
In some embodiments, $R^1$ is
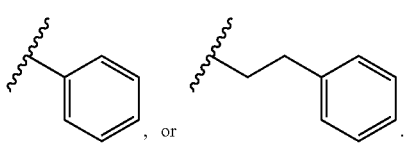 [SMILES: *c1ccccc1 ; *CCc1ccccc1]
, or .

In some embodiments, $R^1$ is
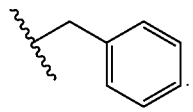
In some embodiments, $R^1$ is
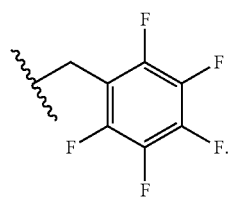 [SMILES: *Cc1c(F)c(F)c(F)c(F)c1F]
In some embodiments, $R^1$ is
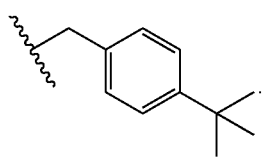 [SMILES: *Cc1ccc(C(C)(C)C)cc1]
In some embodiments, $R^1$ is
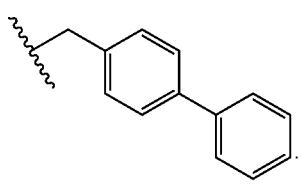 [SMILES: *Cc1ccc(-c2ccccc2)cc1]
In some embodiments, $R^1$ is
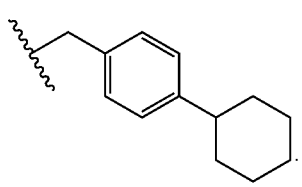 [SMILES: *Cc1ccc(C2CCCCC2)cc1]
In some embodiments, $R^1$ is
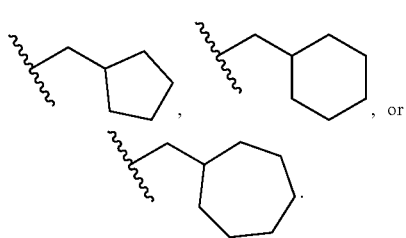
In some embodiments, $R^1$ is
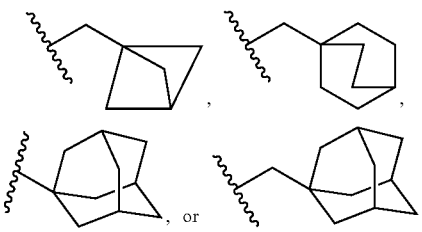
In some embodiments, $R^1$ is
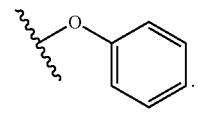
In some embodiments, $R^{2a}$ is
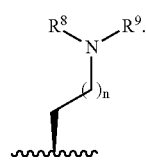
In some embodiments, $R^{2a}$ is
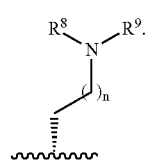
In some embodiments, $R^{2a}$ is
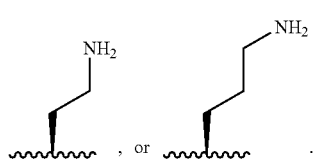
In some embodiments, $R^{2a}$ is
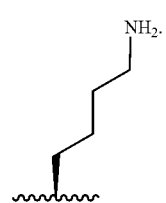

In some embodiments, $R^{2a}$ is

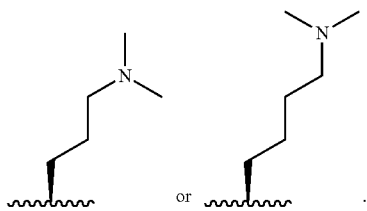

In some embodiments, $R^{2a}$ is

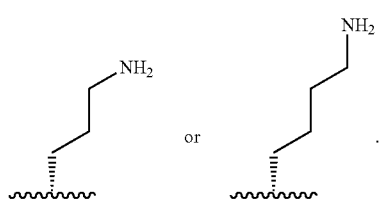

In some embodiments, $R^{2a}$ is

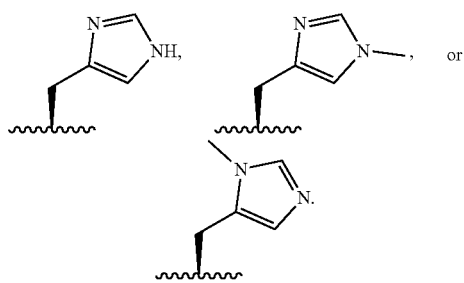

In some embodiments, $R^{2a}$ is

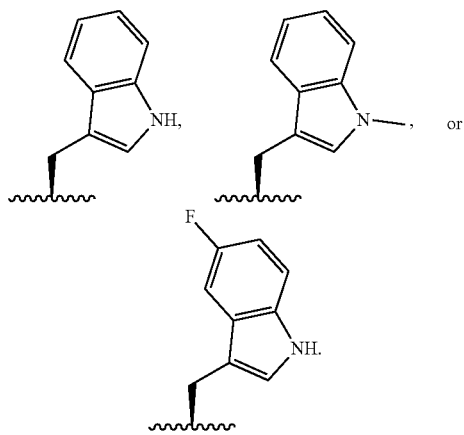

In some embodiments, $R^{2b}$ is H. In some embodiments, $R^{2b}$ is methyl.

In some embodiments, $R^3$ is H. In some embodiments, $R^3$ is $(C_1-C_6)$alkyl. In some embodiments, $R^3$ is methyl, ethyl, n-propyl, i-propyl, n-butyl, i-butyl, or t-butyl. In some embodiments, $R^3$ is methyl. In some embodiments, $R^3$ is ethyl.

In some embodiments, $R^4$ is H. In some embodiments, $R^4$ is $(C_1-C_6)$alkyl. In some embodiments, $R^4$ is methyl, ethyl, n-propyl, i-propyl, n-butyl, i-butyl, or t-butyl. In some embodiments, $R^4$ is methyl. In some embodiments, $R^4$ is ethyl.

In some embodiments, $R^3$ and $R^4$ are the same. In some embodiments, $R^3$ and $R^4$ are different.

In some embodiments, $R^5$ is H. In some embodiments, $R^5$ is methyl.

In some embodiments, $R^6$ is H. In some embodiments, $R^6$ is methyl.

In some embodiments, $R^5$ and $R^6$ are the same. In some embodiments, $R^5$ and $R^6$ are different.

In some embodiments, $R^5$ and $R^6$ together with the N atom to which they are attached form a 4-6-membered heterocyclyl. In some embodiments, the heterocyclyl is a 4-6 membered ring. In some embodiments, the heterocyclyl is azetidinyl, pyrrolidinyl, or piperidinyl.

In some embodiments, $R^7$ is H. In some embodiments, $R^7$ is $(C_1-C_6)$alkyl. In some embodiments, $R^7$ is methyl, ethyl, n-propyl, i-propyl, n-butyl, i-butyl, or t-butyl. In some embodiments, $R^7$ is methyl.

In some embodiments, $R^7$ is cycloalkyl. In some embodiments, $R^7$ is cyclopropyl, cyclobutyl, cyclopropyl, or cyclohexyl. In some embodiments, $R^7$ is aryl. In some embodiments, $R^7$ is phenyl.

In some embodiments, $R^8$ is H. In some embodiments, $R^8$ is $(C_1-C_6)$alkyl. In some embodiments, $R^8$ is methyl, ethyl, n-propyl, i-propyl, n-butyl, i-butyl, or t-butyl. In some embodiments, $R^8$ is methyl.

In some embodiments, $R^8$ is cycloalkyl. In some embodiments, $R^8$ is cyclopropyl, cyclobutyl, cyclopropyl, or cyclohexyl. In some embodiments, $R^8$ is aryl. In some embodiments, $R^8$ is phenyl.

In some embodiments, $R^9$ is H. In some embodiments, $R^9$ is $(C_1-C_6)$alkyl. In some embodiments, $R^9$ is methyl, ethyl, n-propyl, i-propyl, n-butyl, i-butyl, or t-butyl. In some embodiments, $R^9$ is methyl.

In some embodiments, $R^9$ is cycloalkyl. In some embodiments, $R^9$ is cyclopropyl, cyclobutyl, cyclopropyl, or cyclohexyl. In some embodiments, $R^9$ is aryl. In some embodiments, $R^9$ is phenyl.

In some embodiments, $R^1$ and $R^9$ are the same. In some embodiments, $R^8$ and $R^9$ are different.

In some embodiments, $R^1$ and $R^9$ together with the N atom to which they are attached form a 4-6-membered heterocyclyl. In some embodiments, the heterocyclyl is a 4-6 membered ring. In some embodiments, the heterocyclyl is azetidinyl, pyrrolidinyl, or piperidinyl.

In some embodiments, X is

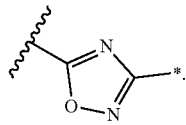

In some embodiments, X is

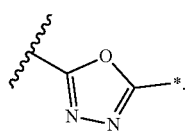

In some embodiments, X is

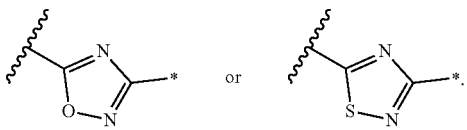

In some embodiments, X is

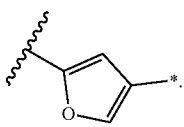

In some embodiments, X is

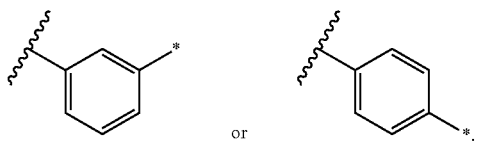

In some embodiments, X is

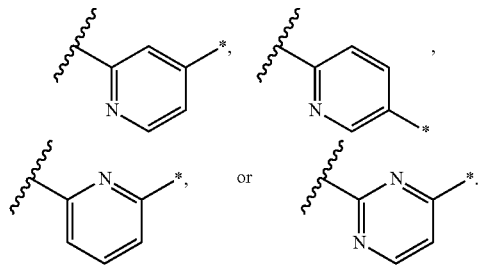

In some embodiments, n is 1. In some embodiments, n is 2. In some embodiments, n is 3.

The chiral centers of the peptidomimetic disclosed herein may be in either the R- or S-configuration as discussed in more detail below.

Chiral/Stereochemistry Considerations

Peptidomimetics described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E.L. Eliel, Ed., Univ. of Notre Dame Press, Notre Dame, Ind. 1972). The peptidomimetics additionally encompasses compounds described herein as individual isomers substantially free of other isomers, and alternatively, as mixtures of various isomers.

R (D for an Amino Acid) or S (L for an Amino Acid)

As used herein, a pure enantiomeric peptidomimetic is substantially free from other enantiomers or stereoisomers of the compound (i.e., in enantiomeric excess). In other words, an "S" form of the compound is substantially free from the "R" form of the compound and is, thus, in enantiomeric excess of the "R" form. With respect to amino acids (which are more commonly described in terms of "D" and "L" enantiomer, it is to be understood that for a "D"-amino acid the configuration is "R" and for an "L"-amino acid, the configuration is "S". In some embodiments, 'substantially free', refers to: (i) an aliquot of an "R" form compound that contains less than 2% "S" form; or (ii) an aliquot of an "S" form compound that contains less than 2% "R" form. The term "enantiomerically pure" or "pure enantiomer" denotes that the compound comprises more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure "R" form compound can comprise, for example, about 90% excipient and about 10% enantiomerically pure "R" form compound. In certain embodiments, the enantiomerically pure "R" form compound in such compositions can, for example, comprise, at least about 95% by weight "R" form compound and at most about 5% by weight "S" form compound, by total weight of the compound. For example, a pharmaceutical composition comprising enantiomerically pure "S" form compound can comprise, for example, about 90% excipient and about 10% enantiomerically pure "S" form compound. In certain embodiments, the enantiomerically pure "S" form compound in such compositions can, for example, comprise, at least about 95% by weight "S" form compound and at most about 5% by weight "R" form compound, by total weight of the compound. In certain embodiments, the active ingredient can be formulated with little or no excipient or carrier.

The nomenclature used to define the peptide compounds described herein is that typically used in the art wherein the amino group at the N-terminus appears to the left and the carboxyl group at the C-terminus appears to the right, provided however that the peptidomimetics disclosed herein do not contain a carboxylic acid moiety or amide moiety at the C-terminus.

A capital letter "D" used in conjunction with an abbreviation for an amino acid residue refers to the D-form of the amino acid residue. For example, D-Arg is a commercially available D-amino acid.

The peptidomimetics disclosed herein can exist in unsolvated forms as well as solvated forms, including hydrated forms. Solvated forms can exist, for example, because it is difficult or impossible to remove all the solvent from the peptidomimetic post synthesis. In general, the solvated forms are equivalent to unsolvated forms and are encompassed within the scope of the present application. Certain peptidomimetics of the present application may exist in multiple crystalline or amorphous forms. Certain peptidomimetics of the present application may exist in various tautomeric forms. Certain peptidomimetics of the present application may exist in various salt forms. In general, all physical forms are equivalent for the uses contemplated by the present application and are intended to be within the scope of the present application.

In some embodiments, the mitochondria-targeting peptidomimetics disclosed herein, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri-(tris-) acid salt), monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a tri-hydrochloride salt (e.g., (Ia)), a mono-tosylate salt, a bis-tosylate salt, or a tri-tosylate salt, are for use in treating or preventing ALS, α-synucleinopathies, or TDP-43 proteinopathies in a subject in need thereof. In some embodiments, the mitochondria-targeting peptidomimetic is (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (e.g., (Ia)). In some embodiments, the subject has been diagnosed as having ALS, an α-synucleinopathy or a TDP-43 proteinopathy.

In other embodiments, the mitochondria-targeting peptidomimetics disclosed herein, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri-(tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a tri-hydrochloride salt (e.g., (Ia)), a mono-tosylate salt, a bis-tosylate salt, or a tri-tosylate salt,) are for use in improving muscle weakness, muscle wasting (atrophy), muscle fasciculations, muscle spasticity, slowness of movement, poor balance, incoordination, alterations in vocal quality, dysarthria, dysphagia, incomplete eye closure, drooling, pseudobulbar affect, survival, increased brain translocator protein-18 kDa (TSPO) expression, and plasma accumulation of NfL in a subject having ALS. In some embodiments, the mitochondria-targeting peptidomimetic is (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (e.g., (Ia)). In some embodiments, the subject has been diagnosed as having ALS.

In some embodiments of the mitochondria-targeting peptidomimetics of the present technology, the treating or preventing comprises the treatment or prevention of one or more signs or symptoms of ALS comprising one or more of muscle weakness, muscle wasting (atrophy), muscle fasciculations, muscle spasticity, slowness of movement, poor balance, incoordination, alterations in vocal quality, dysarthria, dysphagia, incomplete eye closure, drooling, pseudobulbar affect, premature death, increased brain translocator protein-18 kDa (TSPO) expression, and plasma accumulation of NfL. In some embodiments, the treating or preventing refers to a delay in the onset of neurological symptoms of ALS as assessed by neurological scoring as described herein.

In some embodiments of the peptidomimetics of the present technology, the mitochondria-targeting peptidomimetic is intended or formulated to be administered to the subject separately, sequentially, or simultaneously with an additional therapeutic agent or an additional therapeutic treatment. In some embodiments, the additional therapeutic agent is selected from the group consisting of: riluzole (Rilutek®), edaravone (Radicava®), mecasermin, baclofen (Lioresal®), diazepam (Valium®), dantrolene (Dantrium®), nonsteroidal anti-inflammatory agents, anticonvulsive medications (e.g., carbamazepine (Tegretol) or phenytoin (Dilantin®)), amitriptyline (Elavil®), nortriptyline (Pamelor™), and Lorazepam (Ativan®). In some embodiments, the therapeutic agent is elamipretide (also known as SS-31 or bendavia). In some embodiments, the peptidomimetics are for use wherein the combination of peptidomimetic and an additional therapeutic agent or treatment has a synergistic effect in the prevention or treatment of ALS. In some embodiments, the additional therapeutic agent is levodopa. In some embodiments, the peptidomimetics are for use wherein the combination of peptidomimetic an additional therapeutic agent or treatment has a synergistic effect in the prevention or treatment of α-synucleinopathies. In some embodiments, the additional therapeutic agent is an antidepressant such as a selective serotonin reuptake inhibitor (SSRI), including trazodone. In some embodiments, the peptidomimetics are for use wherein the combination of peptidomimetic an additional therapeutic agent or treatment has a synergistic effect in the prevention or treatment of TDP-43 proteinopathies.

Synthesis of Mitochondria-Targeting Peptidomimetics

The peptidomimetic compounds of the present technology may be prepared, in whole or in part using a peptide synthesis methods, such as conventional liquid-phase (also known as solution-phase) peptide synthesis or solid-phase peptide synthesis, or by peptide synthesis by means of an automated peptide synthesizer (Kelley et al., Genetics Engineering Principles and Methods, Setlow, J. K. eds., Plenum Press NY. (1990) Vol. 12, pp. 1 to 19; Stewart et al., Solid-Phase Peptide Synthesis (1989) W. H.; Houghten, Proc. Natl. Acad. Sci. USA (1985) 82: p. 5132). The peptidomimetic thus produced can be collected or purified by a routine method, for example, chromatography, such as gel filtration chromatography, ion exchange column chromatography, affinity chromatography, reverse phase column chromatography, and HPLC, ammonium sulfate fractionation, ultrafiltration, and immunoadsorption.

In a solid-phase peptide synthesis, peptides are typically synthesized from the carbonyl group side (C-terminus) to amino group side (N-terminus) of the amino acid chain. In certain embodiments, an amino-protected amino acid is covalently bound to a solid support material through the carboxyl group of the amino acid, typically via an ester or amido bond and optionally via a linking group. The amino group may be deprotected and reacted with (i.e., "coupled" with) the carbonyl group of a second amino-protected amino acid using a coupling reagent, yielding a dipeptide bound to a solid support. After coupling, the resin is optionally treated with a capping reagent to thereby cap (render inactive towards subsequent coupling steps) any unreacted amine groups. These steps (i.e., deprotection, coupling and optionally capping) may be repeated to form the desired peptide chain. Once the desired peptide chain is complete, the peptide may be cleaved from the solid support.

In certain embodiments, the protecting groups used on the amino groups of the amino acid residues (of peptides and/or peptidomimetics) include 9-fluorenylmethyloxycarbonyl group (Fmoc) and t-butyloxycarbonyl (Boc). The Fmoc group is removed from the amino terminus with base while the Boc group is removed with acid. In alternative embodiments, the amino protecting group may be formyl, acrylyl (Acr), benzoyl (Bz), acetyl (Ac), trifluoroacetyl, substituted or unsubstituted groups of aralkyloxycarbonyl type, such as the benzyloxycarbonyl (Z), p-chlorobenzyloxycarbonyl, p-bromobenzyloxycarbonyl, p-nitrobenzyloxycarbonyl, p-methoxybenzyloxycarbonyl, benzhydryloxycarbonyl, 2(p-biphenylyl)isopropyloxycarbonyl, 2-(3,5-dimethoxyphenyl)isopropyloxycarbonyl, p-phenylazobenzyloxycarbonyl, triphenylphosphonoethyloxycarbonyl or 9-fluorenylmethyloxycarbonyl group (Fmoc), substituted or unsubstituted groups of alkyloxycarbonyl type, such as the tert-butyloxycarbonyl (BOC), tert-amyloxycarbonyl, diisopropylmethyloxycarbonyl, isopropyloxycarbonyl, ethyloxycarbonyl, allyloxycarbonyl, 2 methylsulphonylethyloxycarbonyl or 2,2,2-trichloroethyloxycarbonyl group, groups of cycloalkyloxycarbonyl type, such as the cyclopentyloxycarbonyl, cyclohexyloxycarbonyl, adamantyloxycarbonyl or isobornyloxycarbonyl group, and groups containing a hetero atom, such as the benzenesulphonyl, p-toluenesulphonyl, mesitylenesulphonyl, methoxytrimethylphenylsulphonyl, 2-nitrobenzenesulfonyl, 2-nitrobenzenesulfenyl, 4-nitrobenzenesulfonyl or 4-nitrobenzenesulfenyl group.

Many amino acids bear reactive functional groups in the side chain. In certain embodiments, such functional groups are protected in order to prevent the functional groups from reacting with the incoming amino acid. The protecting groups used with these functional groups must be stable to the conditions of peptide and/or peptidomimetic synthesis, but may be removed before, after, or concomitantly with cleavage of the peptide from the solid support (if support bound) or upon final deprotection in the case of solution-phase synthesis. Further reference is also made to: Isidro-Llobet, A., Alvarez, M., Albericio, F., "Amino Acid-Protecting Groups"; Chem. Rev., 109: 2455-2504 (2009) as a comprehensive review of protecting groups commonly used in peptide synthesis (which protection groups can also be used in peptidomimetic synthesis where the peptidomimetic comprises functional groups found in peptides).

In certain embodiments, the solid support material used in the solid-phase peptide synthesis method is a gel-type support such as polystyrene, polyacrylamide, or polyethylene glycol. Alternatively, materials such as controlled-pore glass, cellulose fibers, or polystyrene may be functionalized at their surface to provide a solid support for peptide synthesis.

Coupling reagents that may be used in the solid-phase (or solution-phase) peptide synthesis described herein are typically carbodiimide reagents. Examples of carbodiimide reagents include, but are not limited to, N,N'-dicyclohexylcarbodiimide (DCC), 1-(3-dimethylaminopropyl)-3-ethylcarbodiimide (EDC) and its HCl salt (EDC.HCl), N-cyclohexyl-N'-isopropylcarbodiimide (CIC), N,N'-diisopropylcarbodiimide (DIC), N-tert-butyl-N'-methylcarbodiimide (BMC), N-tert-butyl-N'-ethylcarbodiimide (BEC), bis[[4-(2,2-dimethyl-1,3-dioxolyl)]-methyl]carbodiimide (BDDC), and N,N-dicyclopentylcarbodiimide. DCC is a preferred coupling reagent. Other coupling agents include HATU and HBTU, generally used in combination with an organic base such as DIEA and a hindered pyridine-type base such as lutidine or collidine.

In some embodiments, the amino acids can be activated toward coupling to a peptide or peptidomimetic by forming N-carboxyanhydrides as described in Fuller et al., Urethane-Protected α-Amino Acid N-Carboxyanhydrides and Peptide Synthesis, Biopolymers (Peptide Science), Vol. 40, 183-205 (1996) and WO2018/034901.

In certain exemplary embodiments, compounds useful in the therapeutic methods described herein can be synthesized in a convergent fashion, according to the solid phase synthesis depicted in Scheme 1.

For reference in the following schemes,

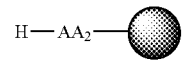

indicates

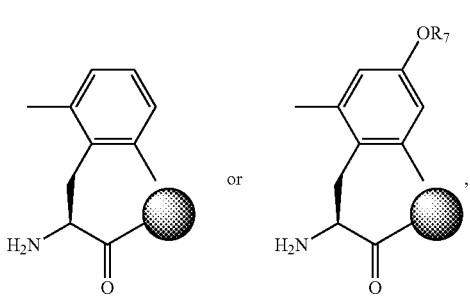

wherein ● represents a solid support and optionally a linking group.

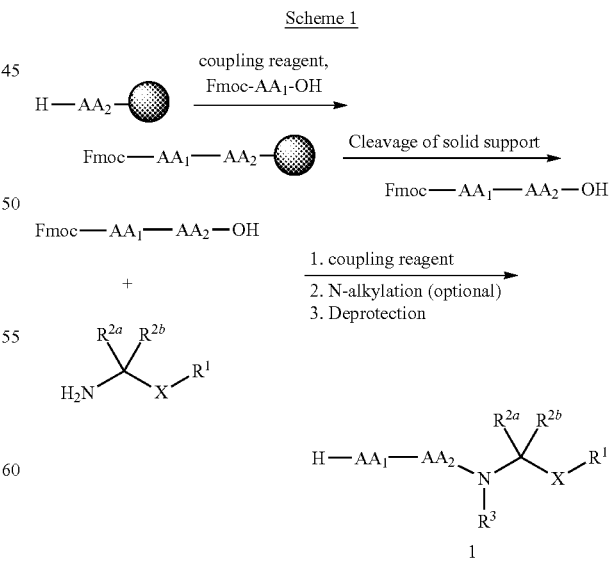

For example, the compound pictured below may be synthesized in such a fashion, as illustrated in Scheme 2.

Scheme 2

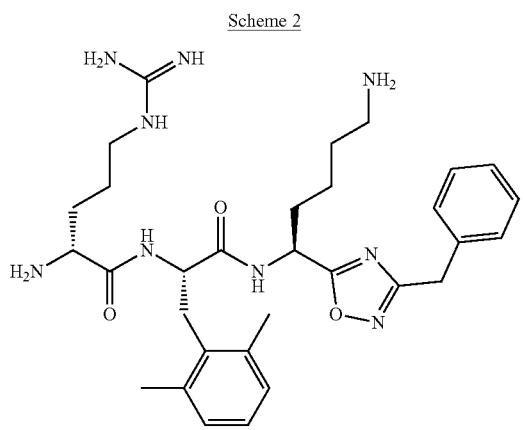 [SMILES: Cc1cccc(C)c1C[C@H](NC(=O)[C@H](N)CCCNC(=N)N)C(=O)N[C@@H](CCCCN)c1nc(Cc2ccccc2)no1]

For reference in the following schemes,

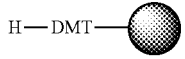

indicates

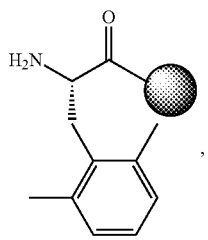

wherein ● represents a solid support and optionally a linking group.

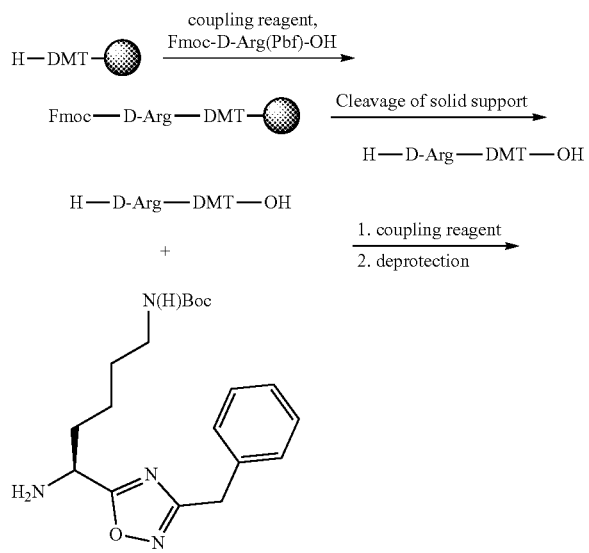

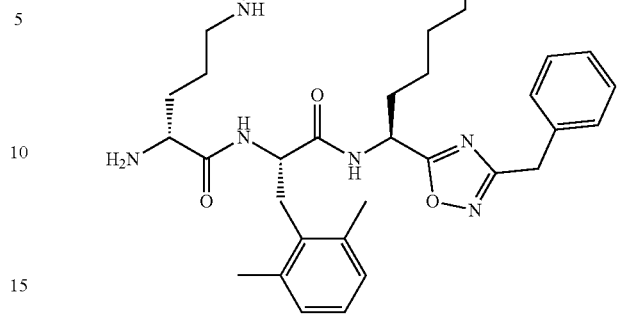

The compounds of the present technology may also be synthesized according to conventional liquid-phase peptide synthetic routes, e.g., according to Scheme 3.

Scheme 3

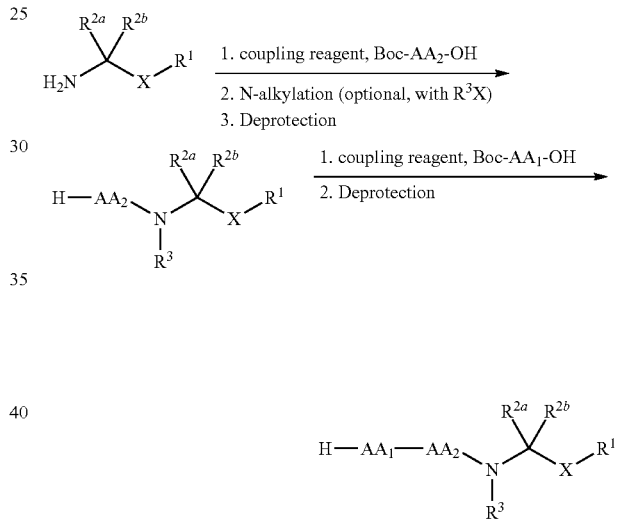

For example, the compound pictured below may be synthesized in such a fashion, as illustrated in Scheme 4.

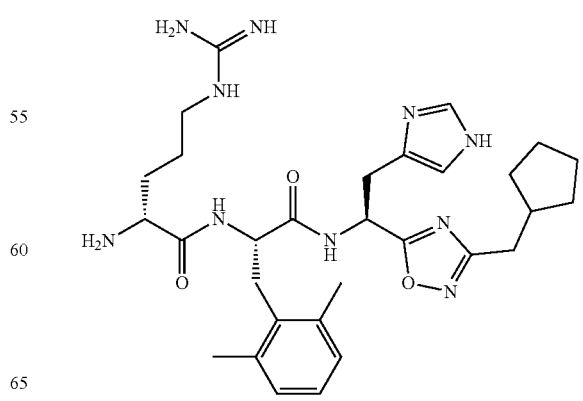

Scheme 4

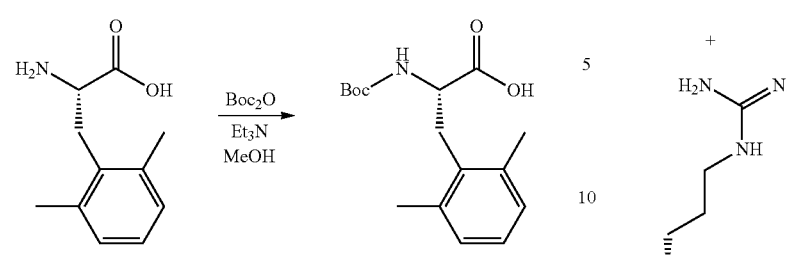

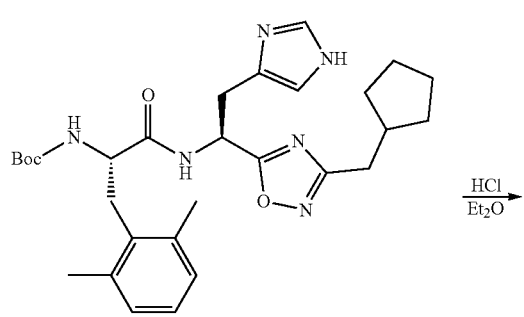

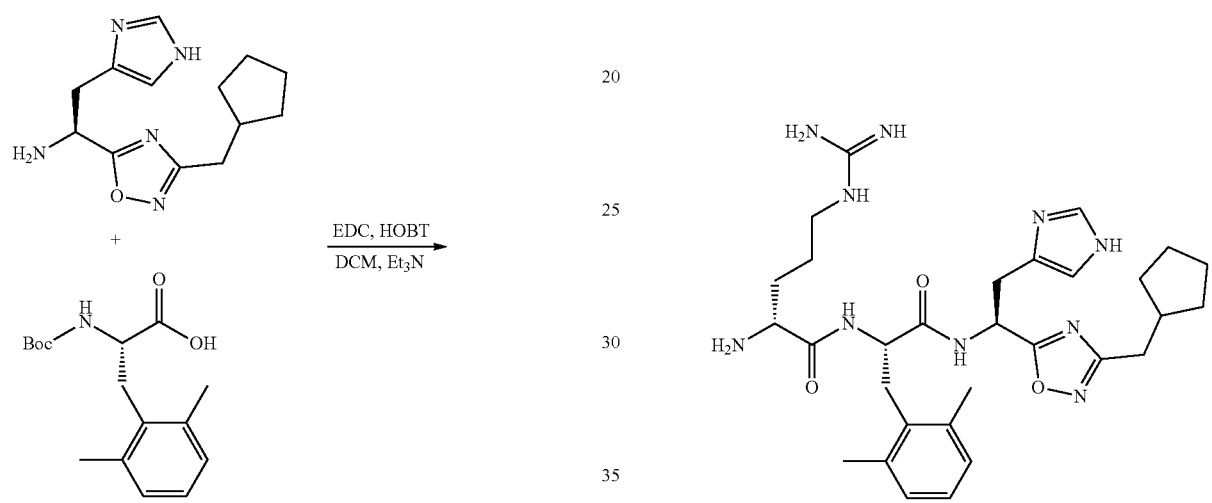

Synthesis of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (D-Arg-DMT-NH((S)-5-amino-1-(3-benzyl-1,2,4-oxadiazol-5-yl)pent-1-yl), 7a)

In some embodiments, Compound 7a may be synthesized as illustrated in Scheme 5, below (Also see WO2019/118878, incorporated herein by reference), wherein compound 12a can be prepared as illustrated in Scheme 6, below.

Compound 7a

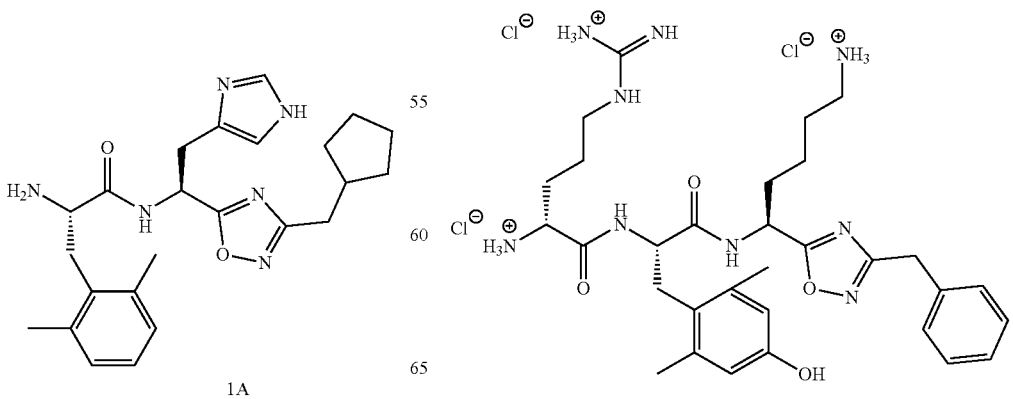

Scheme 5

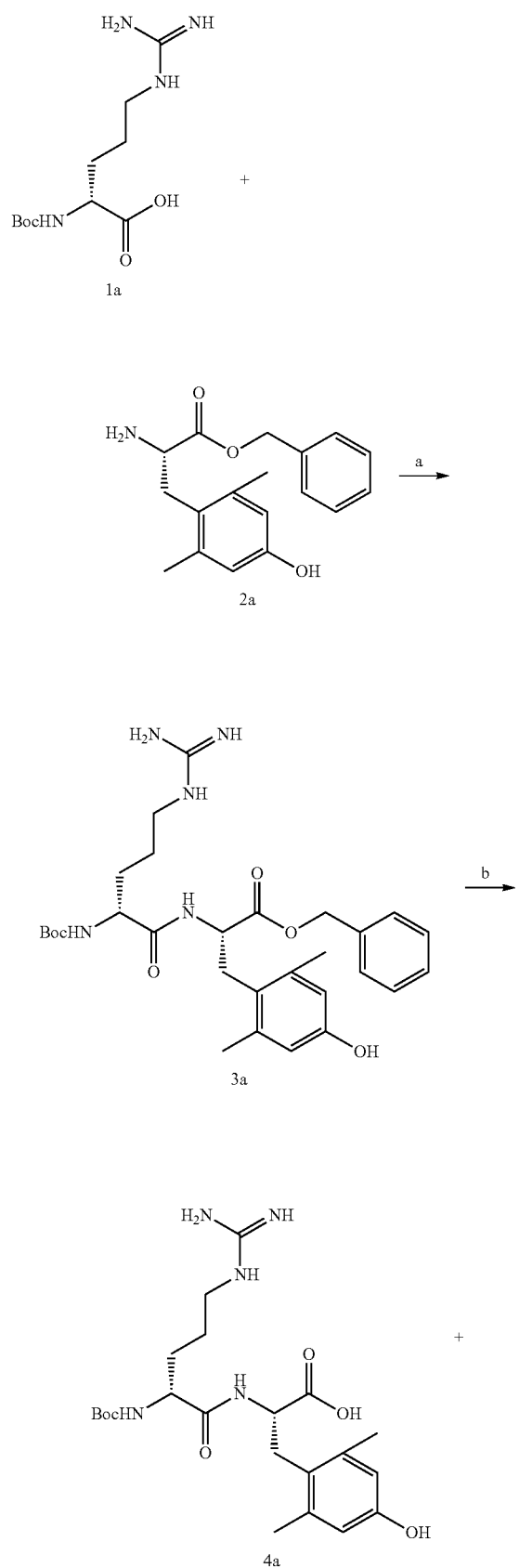

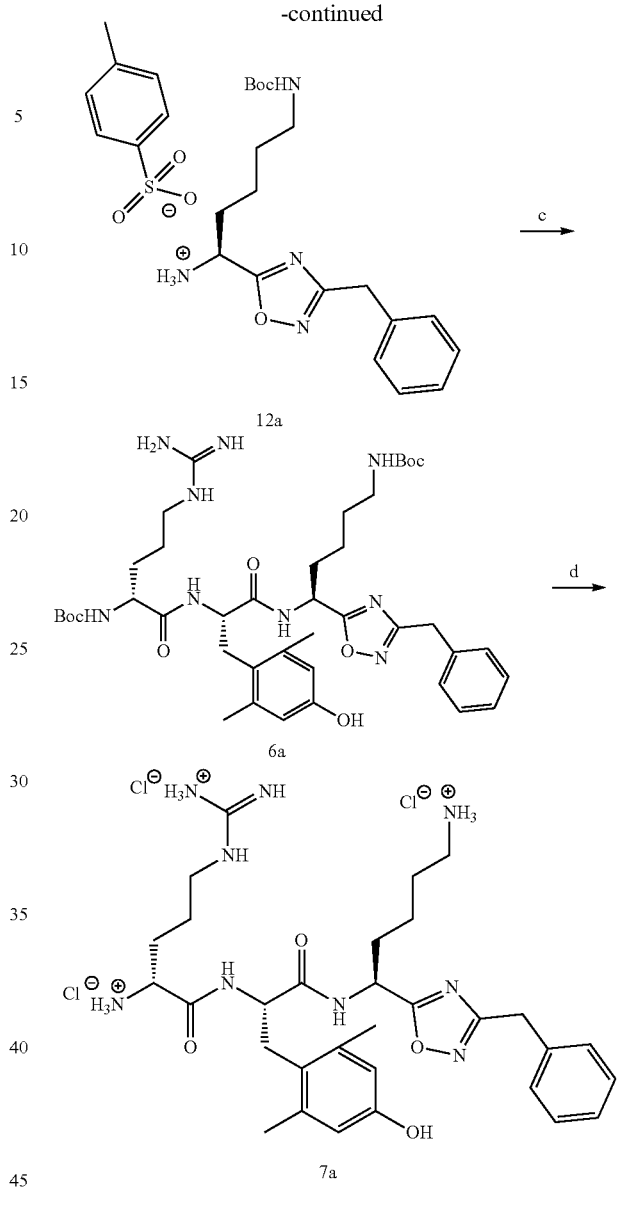

Step a: Synthesis of benzyl (S)-2-((R)-2-((tert-butoxycarbonyl)amino)-5-guanidinopentanamido)-3-(4-hydroxy-2,6-dimethylphenyl)propanoate (3a). To a suspension of 2,6-Dmt-OBn.HCl (2a, 45.0 g, 134 mmol) in ACN (800 mL), NMM (32.7 mL, 298 mmol) was added at 0° C. The reaction mixture was stirred until the reaction mixture became transparent. Then Boc-D-Arg-OH.HCl (1a, 46.3 g, 149 mmol) and HOBt.H$_2$O (9.11 g, 59.5 mmol) were added to reaction mixture and stirred for 15 min. Finally, EDC.HCl (38.5 g, 201 mmol) was added and mixture was stirred at 0° C. for 4 h. Then EtOAc (450 mL), 1N HCl in brine (300 mL) were added. The combined organic extracts were washed with 1N HCl in brine (7×150 mL), NaHCO$_3$/brine (300 mL and until pH of aqueous layer is about pH=6 to 7), dried over Na$_2$SO$_4$, filtered and concentrated to afford 86.0 g (97%) of Boc-D-Arg-DMT-OBn (3a) that was used without further purification. $^1$H-NMR (400 MHz, Methanol-d$_4$) δ 7.33-7.18 (m, 5H), 6.43 (s, 2H), 5.06 (s, 2H) 4.71 (t, J=7.8 Hz, 1H), 4.07 (t, J=6.7 Hz, 1H), 3.19-3.09 (m, 3H), 3.03-2.97 (m, 1H), 2.23 (s, 6H), 1.72-1.65 (m, 1H), 1.54-1.43 (m, 3H), 1.45 (s, 9H).

Step b: Synthesis of (S)-2-((R)-2-((tert-butoxycarbonyl)amino)-5-guanidinopentanamido)-3-(4-hydroxy-2,6-dimethylphenyl)propanoic acid (4a). To a solution of Boc-D-Arg-DM-Tyr-OBn (3a, 84.0 g, 142 mmol) in MeOH (1000 mL) Pd/C (10% w/w, 14.0 g) was added. The hydrogen was purged in reaction mixture at room temperature for 4h. Then reaction mixture was filtrated through filter paper and washed with MeOH (150 mL). The solvent was removed by evaporation. White foam product 4a was obtained (74.0 g, 93%) and used without further purification. $^1$H-NMR (400 MHz, Methanol-d$_4$) δ 6.44 (s, 2H), 4.68 (t, J=7.2 Hz, 1H), 4.04 (t, J=6.8 Hz, 1H), 3.15-3.09 (m, 3H), 3.02-2.94 (m, 1H), 2.29 (s, 6H), 1.74-1.59 (m, 1H), 1.54-1.43 (m, 1H), 1.45 (s, 9H).

Step c: Synthesis of tert-butyl ((6R,9S,12S)-1-amino-12-(3-benzyl-1,2,4-oxadiazol-5-yl)-9-(4-hydroxy-2,6-dimethylbenzyl)-1-imino-20,20-dimethyl-7,10,18-trioxo-19-oxa-2,8,11,17-tetraazahenicosan-6-yl)carbamate (6a). DMF (200 mL) was added to 4a (11.17 g, 24 mmol) and stirred at r.t. for 15 min. To the resulting suspension, 12a (10.65 g, 20 mmol) was added and stirred at r.t. for 20 min. After addition of HOBt (612 mg, 4.00 mmol), the suspension was cooled in ice bath. EDC HCl (5.38 g, 28 mmol) was added in one portion, and the reaction mixture was stirred while cooled in ice bath for 2.5 h and, then, for 4.5 h at r.t. The nearly homogeneous reaction mixture was quenched with EtOAc (1500 mL) and the resulting solution was washed for 10 times with brine/aq. 0.5 M HCl (1:1; 400 mL). During the 6th and 9th washings, gel in the aqueous phase was formed. After addition of iPrOH (40 mL in each case) and repeated shaking the layers went clear again. Afterwards, the organic phase was washed for 6 times with brine/sat. aq. NaHCO$_3$ (9:1; 400 mL). During the 4th washing, gel in the aqueous phase was formed. After addition of iPrOH (40 mL) and repeated shaking the layers were separated easily. The organic phase was washed with brine (200 mL) and water (100 mL) and the solvent was removed under reduced pressure. No vigorous shaking was performed upon washing with water to avoid difficulties in phase separation. As a result, 16.8 g of the crude product were obtained (6a, 97.0% purity by HPLC, white amorphous solid). $^1$H-NMR (300 MHz, Methanol-d$_4$) ppm: δ=7.33-7.16 (m, 5H), 6.38 (s, 2H), 5.18-5.07 (m, 1H), 4.64-4.55 (m, 1H), 4.10-3.92 (m, 3H), 3.18-2.77 (m, 6H), 2.20 (s, 6H), 1.97-1.76 (m, 2H), 1.75-1.14 (m, 8H), 1.43 (s, 9H), 1.41 (s, 9H).

Step d: Synthesis of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (7a, but also referred to as (Ia the tri-hydrochloride salt of Compound I) herein). After 6a (16.8 g) was dissolved in DCM (100 mL) and cooled to 0° C., TFA (20 mL) was added dropwise and the solution was allowed to stir at 0° C. for 10 min, and then at r.t. for 3 h (LC/MS shows no starting material). Then reaction mixture was evaporated (at 0-5° C.) and additionally re-evaporated from DCM (100 mL, at 0-5° C.). The purification by flash chromatography on reverse phase (cartridge C-18, 120G) was performed on crude material divided in 4 parts. Then all solvents were evaporated at reduced pressure at <40° C. White foam was dissolved in isopropanol (100 mL) and 5 mL of HCl in isopropanol (5-6M) was added at 0° C. and evaporated under reduced pressure. This step was repeated 3 times. Additionally, 100 mL of ACN was added and suspension was evaporated one more time. As a result, white powder of 7a was obtained as the tri-hydrochloride salt. $^1$H-NMR (300 MHz, Methanol-d$_4$) δ 7.36-7.14 (m, 5H), 6.40 (s, 2H), 5.15 (dd, J=8.5, 6.3 Hz, 1H), 4.68 (dd, J=8.7, 7.5 Hz, 1H), 4.07 (s, 2H), 3.97 (t, J=6.3 Hz, 1H), 3.18 (t, J=6.9 Hz, 2H), 3.11 (dd, J=14.2, 8.8 Hz, 1H), 2.95-2.84 (m, 3H), 2.22 (s, 6H), 2.02-1.59 (m, 6H), 1.57-1.28 (m, 4H). MS: EI-MS: m/z 608.4 [M+1].

Synthesis of (S)-1-(3-Benzyl-1,2,4-oxadiazol-5-yl)-5-((tert-Butoxycarbonyl)amino)pentan-1-Aminium 4-Methylbenzenesulfonate (12a)

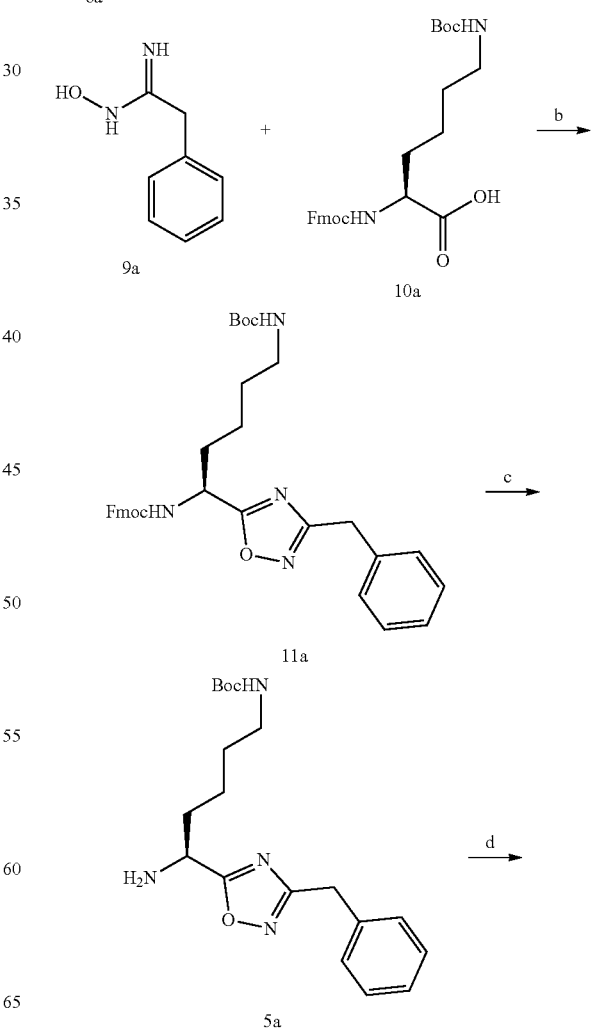

Scheme 6

-continued

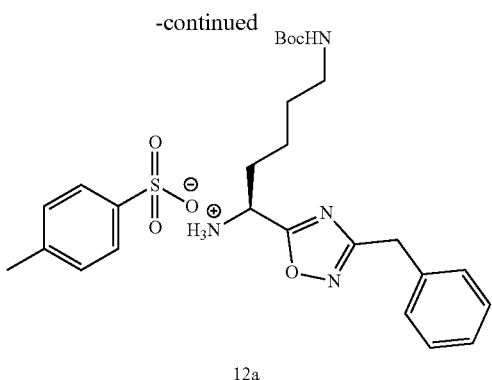

12a step a: NH$_2$OH; step b: T$_3$P, NaHCO$_3$; step c: TEA; step d: PTSA

Step a: Synthesis of N-hydroxy-2-phenylacetimidamide (9a). To a solution of nitrile 8a (1.0 mol) in EtOH (1.2 L) was added NH$_2$OH (50% aqueous solution, 130 g, 2.0 mol). The solution was heated to reflux and stirred for 12 hours (hrs.). After completion, the reaction mixture was concentrated under reduced pressure. The resulting residue was re-dissolved in EtOH (350 mL) and concentrated under reduced pressure again (this procedure was repeated three times). The resulting solid was triturated in hexane (350 mL), filtered, washed with hexane (100 mL), and then dried to give the desired product 9a as white solid. (10.5 kg; KF=1295) with good results (purity by HPLC, >98.9 A %; Assay=22.2 w %, yield=91%). $^1$H NMR (300 MHz, DMSO-d$_6$): δ 8.90 (s, 1H), 7.28-7.18 (m, 5H), 5.40 (s, 2H), 3.25 (s, 2H) ppm. MS: (M+H)$^+$: m/z=151.1

Step b: Synthesis of (9H-Fluoren-9-yl)methyl tert-Butyl (1-(3-Benzyl-1,2,4-oxadiazol-5-yl)pentane-,5-diyl) (S)-Dicarbamate (IIa). To a solution of protected enantiomerically pure N2-(((9H-fluoren-9-yl)methoxy)carbonyl)-N6-(tert-butoxycarbonyl)-L-lysine (10a, 4.31 kg, 9.2 mol) and hydroxyimidamide 9a (1.1 equivalents "equiv." or "eq.") in ethyl acetate was added NaHCO$_3$ (3.0 equiv.). The mixture was stirred at 25° C. for 20 minutes (min.). Then, propane phosphonic acid anhydride (T$_3$P, 50% solution in ethyl acetate, 3.0 equivalents (equiv.)) was added and the reaction mixture was heated to 80° C. and stirred for 4 hrs. (about 60% conversion of compound 10a based on HPLC). Then compound 9a (1.1 equiv.) was added and the reaction mixture was stirred at 80° C. for another 20 hr. (about 10% compound 10a remained). The reaction mixture was cooled to room temperature, saturated aqueous NaHCO$_3$ (2.0 L) was added, the mixture was then extracted with ethyl acetate (3×1.0 L). The combined organic layers were then washed with brine (1 L), dried over anhydrous Na$_2$SO$_4$, filtered and concentrated to give a crude residue, which was generally purified by silica gel column chromatography (Petroleum ether (PE):EtOAc=5:1) to give crude product, (9H-fluoren-9-yl)methyl tert-butyl (1-(3-benzyl-1,2,4-oxadiazol-5-yl)pentane-1,5-diyl) (S)-dicarbamate (11a), solution in ACN (19.7 kg, assay=20%, chiral HPLC purity=99.12 A %, yield=73%). $^1$H-NMR (300 MHz, CDCl$_3$): δ 7.78 (d, J=7.5 Hz, 2H), 7.61 (d, J=6.3 Hz, 2H), 7.42 (t, J=7.5 Hz, 2H), 7.35-7.30 (m, 7H), 5.52 (br, 1H), 5.09-5.05 (m, 1H), 4.56-4.37 (m, 3H), 4.22 (t, J=6.6 Hz, 1H), 4.08 (s, 2H), 1.95-1.86 (m, 2H), 1.48-1.42 (m, 11H) ppm. MS: (M−100+H)$^+$: m/z=483.2.

Step c: Synthesis of tert-Butyl (S)-(5-Amino-5-(3-Benzyl-1,2,4-oxadiazol-5-yl)pentyl)-carbamate (5a). To a solution of compound (9H-fluoren-9-yl)methyl tert-butyl (1-(3-benzyl-1,2,4-oxadiazol-5-yl)pentane-1,5-diyl) (S)-dicarbamate (11a) was added TEA (2.5 eq.). The mixture was kept stirring with mechanical stirrer at 20-25° C. for 15 h. The reaction mixture was diluted by tap water and MTBE. Separated, aqueous layer was extracted by MTBE for one time. Both MTBE layers were combined, and then washed by NH$_4$Cl. Then anhydrous Na$_2$SO$_4$ was added and that solution stirred for least 2 h, then filtered and washed with MTBE to afford tert-butyl (S)-(5-amino-5-(3-benzyl-1,2,4-oxadiazol-5-yl)pentyl)-carbamate (5a) solution in MTBE (32.9 kg, assay=6.5%, yield=88%). $^1$H-NMR (300 MHz, DMSO-d$_6$): δ 7.33-7.25 (m, 5H), 6.78 (br, 1H), 5.09-5.05 (m, 1H), 4.56-4.37 (m, 3H), 4.06 (s, 2H), 3.98 (t, J=6.6 Hz, 1H), 2.87-2.84 (m, 2H), 2.10 (s, 2H), 1.38-1.34 (m, 2H), 1.24 (s, 9H), 1.20-1.15 (m, 2H) ppm. MS: (M+H)$^+$: m/z=361.1.

Step d: Synthesis of (S)-1-(3-Benzyl-1,2,4-oxadiazol-5-yl)-5-((tert-Butoxycarbonyl)-amino)pentan-1-Aminium 4-Methylbenzenesulfonate (12a). p-toluenesulfonic acid (PTSA) was added to solution of crude tert-butyl (S)-(5-amino-5-(3-benzyl-1,2,4-oxadiazol-5-yl)pentyl)-carbamate (5a) in MTBE to afford (S)-1-(3-benzyl-1,2,4-oxadiazol-5-yl)-5-((tert-butoxycarbonyl)amino)pentan-1-aminium 4-methylbenzenesulfonate (12a) (2.7 kg, yield=85%, HPLC purity >99%, ee >99%) as white solid. $^1$H-NMR (400 MHz, DMSO-d$_6$): δ 8.74 (br, 3H), 7.48 (d, J=8.0 Hz, 2H), 7.37-7.26 (m, 5H), 7.11 (d, J=8.0 Hz, 2H), 6.77 (t, J=5.2 Hz, 1H), 4.82 (t, J=6.8 Hz, 1H), 4.17 (s, 2H), 2.90-2.86 (m, 2H), 2.29 (s, 3H), 1.39-1.36 (m, 11H), 1.35-1.28 (m, 2H) ppm. MS: (M−172+H)$^+$: m/z=361.1.

Therapeutic Methods

The following discussion is presented by way of example only, and is not intended to be limiting.

One aspect of the present technology includes methods of treating ALS, α-synucleinopathies, or TDP-43 proteinopathies in a subject diagnosed as having, suspected as having, or at risk of having ALS, α-synucleinopathies, or TDP-43 proteinopathies. In therapeutic applications, compositions or medicaments comprising mitochondria-targeting peptidomimetic, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri-(tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia), a mono-tosylate salt, a bis-tosylate salt, or a tri-tosylate salt) are administered to a subject suspected of, or already suffering from ALS, an α-synucleinopathy, or a TDP-43 proteinopathy in an amount sufficient to cure, or at least partially arrest, the symptoms of the disease, including its complications and intermediate pathological phenotypes in development of the disease. In some embodiments of the methods of the present technology, the mitochondria-targeting peptidomimetic is (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (e.g., (Ia)).

Other aspects of the present technology include uses of a composition in the preparation of a medicament for treating or preventing ALS, α-synucleinopathies, or TDP-43 proteinopathies in a subject in need thereof. The compositions or medicaments comprising mitochondria-targeting peptidomimetic, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt) are suitable for administration to a subject suspected of, or already suffering from ALS, an α-synucleinopathy or a TDP-43 proteinopathy in an amount sufficient to alleviate one or more signs or symptoms of ALS, α-synucleinopathy, or TDP-43 proteinopathy in the subject. In some embodiments of the methods of the present technology, the mitochondria-targeting peptidomimetic is (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (e.g., (Ia)).

Subjects suffering from ALS, α-synucleinopathies, or TDP-43 proteinopathies can be identified by any or a combination of diagnostic or prognostic assays known in the art.

For therapeutic applications, a composition comprising a mitochondria-targeting peptidomimetic, such as 2(R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt) is administered to the subject. In some embodiments, the peptidomimetic composition is administered one, two, three, four, or five times per day. In some embodiments, the peptidomimetic composition is administered more than five times per day. Additionally or alternatively, in some embodiments, the peptidomimetic composition is administered every day, every other day, every third day, every fourth day, every fifth day, or every sixth day. In some embodiments, the peptidomimetic composition is administered weekly, bi-weekly, tri-weekly, or monthly. In some embodiments, the peptidomimetic composition is administered for a period of one, two, three, four, or five weeks. In some embodiments, the peptidomimetic is administered for six weeks or more. In some embodiments, the peptidomimetic is administered for twelve weeks or more. In some embodiments, the peptidomimetic is administered for a period of less than one year. In some embodiments, the peptidomimetic is administered for a period of more than one year or until the signs or symptoms of ALS, α-synucleinopathy, or TDP-43 proteinopathy are alleviated in the subject. In some embodiments, the peptidomimetic is administered according to a physician recommended protocol from the time of diagnosis of the subject as having, suspected as having, or at risk of having ALS, α-synucleinopathies, or TDP-43 proteinopathies until the end of life.

The subject treated in accordance with the present therapeutic methods can be any mammal, including, for example, farm animals, such as sheep, pigs, cows, and horses; pet animals, such as dogs and cats; laboratory animals, such as rats, mice and rabbits. In some embodiments, the mammal is a human.

In some embodiments, treatment of subjects diagnosed with or suspected of having ALS with one or more mitochondria-targeting peptidomimetics ameliorates or eliminates of one or more of the following symptoms of ALS: muscle weakness, muscle wasting (atrophy), muscle fasciculations, muscle spasticity, slowness of movement, poor balance, incoordination, alterations in vocal quality, dysarthria, dysphagia, incomplete eye closure, drooling, pseudobulbar affect, and premature death. In some embodiments, treatment of subjects diagnosed with or suspected of having ALS with one or more mitochondria-targeting peptidomimetics ameliorates or reduces, increased brain translocator protein-18 kDa (TSPO) expression. In some embodiments, treatment of subjects diagnosed with or suspected of having ALS with one or more mitochondria-targeting peptidomimetics ameliorates or eliminates plasma accumulation of NfL. In some embodiments, treatment of subjects diagnosed with or suspected of having ALS with one or more mitochondria-targeting peptidomimetics increases survival/lifespan of the subject. In some embodiments, treatment success with mitochondria-targeting peptidomimetics is determined by detecting an improvement in the subject's symptoms compared to one or more of. (1) a baseline measurement or symptom level detected prior to or with commencement of treatment; (2) a measurement or symptom level from a control subject or a population of control subjects, wherein the control subjects exhibit one or more symptoms of ALS and either (i) have not been administered mitochondria-targeting peptidomimetic, or (ii) have been administered a control peptide or peptidomimetic; or (3) a standard.

In some embodiments, treatment of subjects diagnosed with or suspected of having α-synucleinopathy with one or more mitochondria-targeting peptidomimetics ameliorates or eliminates of one or more of the symptoms of α-synucleinopathy, including but not limited to, the loss of dopaminergic neurons in the subject.

In some embodiments, treatment of subjects diagnosed with or suspected of having TDP-43 proteinopathy with one or more mitochondria-targeting peptidomimetics ameliorates or eliminates of one or more of the symptoms of TDP-43 proteinopathy, including but not limited to, reduced neurite length in the subject.

Prophylactic Methods

In one aspect, the present technology provides a method for preventing or delaying the onset of ALS, α-synucleinopathy, or TDP-43 proteinopathy or one or more symptoms of ALS, α-synucleinopathy, or TDP-43 proteinopathy in a subject at risk of having or developing ALS, α-synucleinopathy, or TDP-43 proteinopathy. In prophylactic applications, pharmaceutical compositions or medicaments of mitochondria-targeting peptidomimetics, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt) are administered to a subject susceptible to, or otherwise at risk of for ALS, α-synucleinopathy, or TDP-43 proteinopathy in an amount sufficient to eliminate or reduce the risk, or delay the onset of the disease, including biochemical, histologic and/or behavioral symptoms of the disease, its complications and intermediate pathological phenotypes presenting during development of the disease. In some embodiments of the methods of the present technology, the mitochondria-targeting peptidomimetic is (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (e.g., (Ia)).

Administration of a prophylactic mitochondria-targeting peptidomimetic can occur prior to the manifestation of symptoms characteristic of the disease or disorder, such that the disease or disorder is prevented or, alternatively, delayed in its progression.

For prophylactic applications, a composition comprising mitochondria-targeting peptidomimetic, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt) is administered to the subject. In some embodiments, the peptidomimetic composition is administered one, two, three, four, or five times per day. In some embodiments, the peptidomimetic composition is administered more than five times per day. Additionally or alternatively, in some embodiments, the peptidomimetic composition is administered every day, every other day, every third day, every fourth day, every fifth day, or every sixth day. In some embodiments, the peptidomimetic composition is administered weekly, bi-weekly, tri-weekly, or monthly. In some embodiments, the peptidomimetic composition is administered for a period of one, two, three, four, or five weeks. In some embodiments, the peptidomimetic is administered for six weeks or more. In some embodiments, the peptidomimetic is administered for twelve weeks or more. In some embodiments, the peptidomimetic is administered for a period of less than one year. In some embodiments, the peptidomimetic is administered for a period of more than one year. In some embodiments, the peptidomimetic is administered according to a physician recommended protocol from the time of diagnosis of the subject as having, suspected as having, or at risk of having ALS, α-synucleinopathies, or TDP-43 proteinopathies until the end of life.

In some embodiments, treatment with the mitochondrial-targeting peptidomimetic will prevent or delay the onset of one or more of the following symptoms: muscle weakness, muscle wasting (atrophy), muscle fasciculations, muscle spasticity, slowness of movement, poor balance, incoordination, alterations in vocal quality, dysarthria, dysphagia, incomplete eye closure, drooling, pseudobulbar affect, and/or premature death. In some embodiments, treatment with the mitochondrial-targeting peptidomimetic will prevent or delay the onset of increased brain translocator protein-18 kDa (TSPO) expression. In some embodiments, treatment with the mitochondrial-targeting peptidomimetic will prevent or delay the onset of plasma accumulation of neurofilament light chain (NfL). In some embodiments, treatment with the mitochondrial-targeting peptidomimetic will prevent or delay premature death. In some embodiments, treatment refers to a delay in the onset of neurological symptoms of ALS as assessed by neurological scoring as described herein.

In some embodiments, treatment with the mitochondrial-targeting peptidomimetic will prevent or delay or attenuate the loss of dopaminergic neurons in the subject.

In some embodiments, treatment with the mitochondrial-targeting peptidomimetic will prevent or delay reduced neurite length in the subject.

The mammal treated in accordance with the present prophylactic methods can be any mammal, including, for example, farm animals, such as sheep, pigs, cows, and horses; pet animals, such as dogs and cats; laboratory animals, such as rats, mice and rabbits. In some embodiments, the mammal is a human.

Determination of the Biological Effect of the Mitochondria-Targeting Peptidomimetic-Based Therapeutic In various embodiments, suitable in vitro or in vivo assays are performed to determine the effect of a specific mitochondria-targeting peptidomimetic-based therapeutic and whether its administration is indicated for treatment. In various embodiments, in vitro assays can be performed with representative animal models, to determine if a given mitochondria-targeting peptidomimetic-based therapeutic exerts the desired effect on reducing or eliminating signs and/or symptoms of ALS, α-synucleinopathy, or TDP-43 proteinopathy.

Animal Models

Compounds for use in therapy can be tested in suitable animal model systems including, but not limited to rats, mice, chicken, cows, monkeys, rabbits, and the like, prior to testing in human subjects. Similarly, for in vivo testing, any of the animal model systems known in the art can be used prior to administration to human subjects. In some embodiments, in vitro or in vivo testing is directed to the biological function of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt). In some embodiments, the animal model is the SOD1 G93A mouse model of ALS. In some embodiments, the animal model is the Sprague Dawley rat. In some embodiments, the animal model is a mutant alpha-synuclein transduced mouse. In some embodiments, the animal model is the prp-TDP-43$^{A315T}$-UeGFP mouse model (Gautam, et al. Acta Neuropathol. 2019 January; 137(1): 47-69).

Modes of Administration and Effective Dosages

Any method known to those in the art for contacting a cell, organ or tissue with a mitochondria-targeting peptidomimetic of the present technology, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g. (Ia)), a mono-tosylate salt, a bis-tosylate salt, or a tri-tosylate salt, an acetate salt, a tartrate salt, a trifluoroacetate salt, a chloride salt, a tris-HCl salt, a bis-HCl salt, a mono-HCl salt, or a tosylate salt) may be employed. In some embodiments of the methods of the present technology, the mitochondria-targeting peptidomimetic is (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (e.g., (Ia)). Suitable methods include in vitro, ex vivo, or in vivo methods. In vivo methods typically include the administration of a mitochondria-targeting peptidomimetic to a mammal, suitably a human. When used in vivo for therapy, the mitochondria-targeting peptidomimetics, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt) are administered to the subject in effective amounts (i.e., amounts that have desired therapeutic effect). The dose and dosage regimen will depend upon the degree of the disease, disorder or condition in the subject, the characteristics of the particular mitochondria-targeting peptidomimetic used, e.g., its therapeutic index, the subject, and the subject's history.

The effective amount may be determined during pre-clinical trials and clinical trials by methods familiar to physicians and clinicians. An effective amount of a peptidomimetic useful in the methods may be administered to a mammal in need thereof by any of a number of well-known methods for administering pharmaceutical compounds. The peptidomimetic may be administered systemically or locally.

The peptidomimetic may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide or peptidomimetic contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-methylmorpholine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, trimethylamine ($NEt_3$), trimethylamine, tripropylamine, tromethamine and the like, such as where the salt includes the protonated form of the organic base (e.g., $[HNEt_3]^+$). Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphorsulfonic, edisylic, ethanesulfonic, isethionic, methanesulfonic, naphthalenesulfonic, naphthalene-1,5-disulfonic, naphthalene-2,6-disulfonic and p-toluenesulfonic acids (PTSA)), xinafoic acid, and the like. In some embodiments, the pharmaceutically acceptable counterion is selected from the group consisting of acetate, benzoate, besylate, bromide, camphorsulfonate, chloride, chlorotheophyllinate, citrate, ethanedisulfonate, fumarate, gluceptate, gluconate, glucoronate, hippurate, iodide, isethionate, lactate, lactobionate, laurylsulfate, malate, maleate, mesylate, methylsulfate, naphthoate, sapsylate, nitrate, octadecanoate, oleate, oxalate, pamoate, phosphate, polygalacturonate, succinate, sulfate, sulfosalicylate, tartrate, tosylate, and trifluoroacetate. In some embodiments, the salt is a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri-(tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt. In some embodiments, the peptidomimetic is formulated as a mono-HCl, bis-HCl salt or a tri- (or tris)-HCl salt (e.g., (Ia)).

The mitochondria-targeting peptidomimetics described herein, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt) can be incorporated into pharmaceutical compositions for administration, singly or in combination, to a subject for the treatment or prevention of a disease, disorder or condition described herein. The peptidomimetic may be formulated with other compounds such as a therapeutic agent, a peptide, another peptidomimetic or mixtures thereof. In some embodiments of the methods of the present technology, the mitochondria-targeting peptidomimetic is (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (e.g., (Ia)). Such compositions typically include the active agent and a pharmaceutically acceptable carrier. In some embodiments, the pharmaceutical compositions can be used as medicaments or in the preparation of medicaments for administration to a subject suffering from ALS, α-synucleinopathies, or TDP-43 proteinopathies. Pharmaceutically acceptable carriers include saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, intravitreal, inhalation, transdermal (topical), intraocular, ophthalmic, intrathecal, intracerebroventricular, iontophoretic, and transmucosal administration. In some embodiments, the route of administration is oral. In some embodiments, the route of administration is subcutaneous. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided alone or in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The mitochondria-targeting peptidomimetic containing compositions can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterates; a glidant such as colloidal silicon dioxide; a sweetening agent such as sucrose or saccharin; or a flavoring agent such as peppermint, methyl salicylate, or orange flavoring.

One may dilute or increase the volume of a compound, therapeutic agent, peptide, peptidomimetic or mixtures thereof with an inert material. These diluents could include carbohydrates, especially mannitol, lactose, anhydrous lactose, cellulose, sucrose, modified dextrans and starch. Certain inorganic salts may be also used as fillers including calcium triphosphate, magnesium carbonate and sodium chloride. Some commercially available diluents are Fast-Flo, Emdex, STA-Rx 1500, Emcompress and Avicel.

Disintegrants may be included in the formulation of compound, therapeutic agent, peptide, peptidomimetic or mixtures thereof with an inert material into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders, and these can include powdered gums such as agar, Karaya or tragacanth. Alginic acid and its sodium salt are also useful as disintegrants.

Binders may be used to hold a compound, therapeutic agent, peptide, peptidomimetic or mixtures thereof with an inert material together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of a compound, therapeutic agent, peptide, peptidomimetic or mixtures thereof to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, fumed silica, pyrogenic silica and hydrated silicoaluminate.

To aid dissolution of a compound, therapeutic agent, peptide, peptidomimetic or mixtures thereof into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound, therapeutic agent, peptide, peptidomimetic or mixtures thereof of the technology or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For administration by inhalation, a compound, therapeutic agent, peptide, peptidomimetic or mixtures thereof for use according to the present application may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In some embodiments, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

A compound, therapeutic agent, peptide, peptidomimetic or mixtures thereof can be delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor; incorporated by reference). A method and composition for pulmonary delivery of drugs for systemic effect is described in U.S. Pat. No. 5,451,569 (incorporated by reference), issued Sep. 19, 1995 to Wong et al.

Contemplated for use in the practice of this technology area wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this technology are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

For ophthalmic or intraocular formulations, any suitable mode of delivering the mitochondria-targeting peptidomimetics described herein (with or without therapeutic agents, peptides or other peptidomimetics, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxo-propan-2-yl)-5-guanidinopentanamide (I), a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt) or pharmaceutical compositions thereof to the eye or regions near the eye can be used. For ophthalmic formulations generally, see Mitra (ed.), *Ophthalmic Drug Delivery Systems*, Marcel Dekker, Inc., New York, N.Y. (1993) and also Havener, W. H., *Ocular Pharmacology*, C.V. Mosby Co., St. Louis (1983). Nonlimiting examples of formulations suitable for administration in or near the eye include, but are not limited to, ocular inserts, minitablets, and topical formulations such as eye drops, ointments, and in situ gels. In one embodiment, a contact lens is coated with the mitochondria-targeting peptidomimetics described herein, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a tri-hydrochloride salt (e.g., (Ia)), a mono-tosylate salt, a bis-tosylate salt, or a tri-tosylate salt). In some embodiments, a single dose comprises from between 0.1 ng to 5000 µg, 1 ng to 500 µg, or 10 ng to 100 g of the mitochondria-targeting peptidomimetics administered to the eye.

Eye drops comprise a sterile liquid formulation that can be administered directly to the eye. In some embodiments, eye drops comprising one or more mitochondria-targeting peptidomimetics described herein, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, monoacetate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a tri-hydrochloride salt (e.g., (Ia)), a mono-tosylate salt, a bis-tosylate salt, or a tri-tosylate salt) further comprise one or more preservatives. In some embodiments, the optimum pH for eye drops equals that of tear fluid and is about 7.4.

In situ gels are viscous liquids, showing the ability to undergo sol-to-gel transitions when influenced by external factors, such as appropriate pH, temperature, and the presence of electrolytes. This property causes slowing of drug drainage from the eyeball surface and increase of the active ingredient bioavailability. Polymers commonly used in in situ gel formulations include, but are not limited to, gellan gum, poloxamer, and cellulose acetate phthalate.

For topical administration, a compound, therapeutic agent, peptide, peptidomimetic or mixtures thereof may be formulated as solutions, gels, ointments, creams, suspensions, etc. as are well-known in the art. Ointments are semisolid dosage forms for external use such as topical use for the eye or skin. In some embodiments, ointments comprise a solid or semisolid hydrocarbon base of melting or softening point close to human core temperature. In some embodiments, an ointment applied to the eye decomposes into small drops, which stay for a longer time period in conjunctival sac, thus increasing bioavailability.

Ocular inserts are solid or semisolid dosage forms without disadvantages of traditional ophthalmic drug forms. They are less susceptible to defense mechanisms like outflow through nasolacrimal duct, show the ability to stay in conjunctival sac for a longer period, and are more stable than conventional dosage forms. They also offer advantages such as accurate dosing of one or more mitochondria-targeting peptidomimetics, slow release of one or more mitochondria-targeting peptidomimetics with constant speed and limiting of one or more mitochondria-targeting peptidomimetics' systemic absorption. In some embodiments, an ocular insert comprises one or more mitochondria-targeting peptidomimetics described herein, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt) and one or more polymeric materials. The polymeric materials include, but are not limited to, methylcellulose and its derivatives (e.g., hydroxypropyl methylcellulose (HPMC)), ethylcellulose, polyvinylpyrrolidone (PVP K-90), polyvinyl alcohol, chitosan, carboxymethyl chitosan, gelatin, and various mixtures of the aforementioned polymers.

Minitablets are biodegradable, solid drug forms, that transit into gels after application to the conjunctival sac, thereby extending the period of contact between active ingredient and the eyeball surface, which in turn increases the active ingredient's bioavailability. The advantages of minitablets include easy application to conjunctival sac, resistance to defense mechanisms like tearing or outflow through nasolacrimal duct, longer contact with the cornea caused by presence of mucoadhesive polymers, and gradual release of the active ingredient from the formulation in the place of application due to the swelling of the outer carrier layers. Minitablets comprise one or more mitochondria-targeting peptidomimetics described herein, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt) and one or more polymers. Nonlimiting examples of polymers suitable for use in in a minitablet formulation include cellulose derivatives, like hydroxypropyl methylcellulose (HPMC), hydroxyethyl cellulose (HEC), sodium carboxymethyl cellulose, ethyl cellulose, acrylates (e.g., polyacrylic acid and its cross-linked forms), Carbopol or Carbomer, chitosan, and starch (e.g., drum-dried waxy maize starch). In some embodiments, minitablets further comprise one or more excipients. Non-limiting examples of excipients include mannitol and magnesium stearate.

The ophthalmic or intraocular preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

In some embodiments, the viscosity of the ocular formulation comprising one or more mitochondria-targeting peptidomimetics described herein, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt) is increased to improve contact with the cornea and bioavailability in the eye. Viscosity can be increased by the addition of hydrophilic polymers of high molecular weight which do not diffuse through biological membranes and which form three-dimensional networks in the water. Nonlimiting examples of such polymers include polyvinyl alcohol, poloxamers, hyaluronic acid, carbomers, and polysaccharides, cellulose derivatives, gellan gum, and xanthan gum.

Systemic administration of a compound, therapeutic agent, peptide, peptidomimetic or mixtures thereof, as described herein, can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A compound, therapeutic agent, peptide, peptidomimetic or mixtures thereof can be formulated in a carrier system. The carrier can be a colloidal system. The colloidal system can be a liposome, a phospholipid bilayer vehicle. In one embodiment, the compound, therapeutic agent, peptide, peptidomimetic or mixtures thereof is encapsulated in a liposome while maintaining integrity of the compound, therapeutic agent, peptide, peptidomimetic or mixtures thereof. One skilled in the art would appreciate that there are a variety of methods to prepare liposomes. (See Lichtenberg, et al., *Methods Biochem. Anal.*, 33:337-462 (1988); Anselem, et al., *Liposome Technology*, CRC Press (1993)). Liposomal formulations can delay clearance and increase cellular uptake (See Reddy, *Ann. Pharmacother.*, 34(7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the compound, therapeutic agent, peptide, peptidomimetic or mixtures thereof can be embedded in the polymer matrix, while maintaining integrity of the composition. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PLGA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi, et al., *Cancer Lett.*, 100: 63-69 (1996), describes the use of fusogenic liposomes to deliver a protein to cells both in vivo and in vitro.

In addition to the formulations described above, compound, therapeutic agent, peptide, peptidomimetic or mixtures thereof may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

A compound, therapeutic agent, peptide, peptidomimetic or mixtures thereof may be provided in particles or polymer microspheres. Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt. The particles may contain the therapeutic agent(s) in a core surrounded by a coating, including, but not limited to, an enteric coating. The compounds, therapeutic agents, peptides, peptidomimetics or mixtures thereof also may be dispersed throughout the particles. The compounds, therapeutic agents, peptides, peptidomimetics or mixtures thereof also may be adsorbed into the particles. The particles may be of any order release kinetics, including zero-order release, first-order release, second-order release, delayed release, sustained release, immediate release, and any combination thereof, etc. The particle may include, in addition to the compounds, therapeutic agents, peptides, peptidomimetics or mixtures thereof, any of those materials routinely used in the art of pharmacy and medicine, including, but not limited to, erodible, nonerodable, biodegradable, or nonbiodegradable material or combinations thereof. The particles may be microcapsules which contain the compound of the technology in a solution or in a semi-solid state. The particles may be of virtually any shape.

Both non-biodegradable and biodegradable polymeric materials can be used in the manufacture of particles for delivering the compounds, therapeutic agents, peptides, peptidomimetics or mixtures thereof. Such polymers may be natural or synthetic polymers. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) and polycaprolactone.

The compounds, therapeutic agents, peptides, peptidomimetics or mixtures thereof may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant (depot) is constructed and arranged to deliver therapeutic levels of the active ingredient (i.e. compound, therapeutic agent, peptide, peptidomimetic or mixtures thereof) for at least 7 days, and preferably 30-60 days. Long-term sustained release implants are well-known to those of ordinary skill in the art and include some of the release systems described above.

Dosage, toxicity and therapeutic efficacy of any compounds, therapeutic agents, peptides, peptidomimetics or mixtures thereof can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the mitochondria-targeting peptidomimetics, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide or peptidomimetic ranges from 0.001-10,000 micrograms per kg body weight. In one embodiment, mitochondria-targeting peptidomimetic concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regimen.

In some embodiments, a therapeutically effective amount of a mitochondria-targeting peptidomimetic may be defined as a concentration of peptidomimetic at the target tissue of $10^{-12}$ to 10-6 molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the compounds, therapeutic agents, peptides, peptidomimetics or mixtures thereof described herein can include a single treatment or a series of treatments.

Combination Therapies

In some embodiments, the mitochondria-targeting peptidomimetics, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt) may be combined with one or more additional therapies for the prevention or treatment of ALS. In some embodiments of the methods of the present technology, the mitochondria-targeting peptidomimetic is (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (e.g., (Ia)). In some embodiments, additional therapies include, but are not limited to, administration of riluzole (Rilutek®), edaravone (Radicava®), mecasermin, baclofen (Lioresal®), diazepam (Valium®), dantrolene (Dantrium®), nonsteroidal anti-inflammatory agents, anticonvulsive medications (e.g., carbamazepine (Tegretol) or phenytoin (Dilantin®)), amitriptyline (Elavil®), nortriptyline (Pamelor™), and Lorazepam (Ativan®). In some embodiments, the additional therapy includes co-administration of elamipretide (a.k.a. SS-31 or Bendavia).

In some embodiments, riluzole is administered separately, simultaneously, or sequentially with the mitochondria-targeting peptidomimetic(s). In some embodiments, the dose of riluzole is about 0.5 mg/kg to about 2 mg/kg, about 1 mg/kg to about 2 mg/kg, about 0.5 mg/kg to about 5 mg/kg, about 5 mg/kg to about 100 mg/kg, about 10 mg/kg to about 75 mg/kg, or about 25 mg/kg to about 50 mg/kg. In some embodiments, the dose of resveratrol is 0.8 mg/kg, about 5 mg/kg, about 10 mg/kg, about 20 mg/kg, about 25 mg/kg, about 30 mg/kg, about 40 mg/kg, about 50 mg/kg, about 60 mg/kg, about 75 mg/kg, about 80 mg/kg, about 90 mg/kg, about 100 mg/kg, about 110 mg/kg, about 120 mg/kg, about 125 mg/kg, about 130 mg/kg, about 140 mg/kg, about 150 mg/kg, about 160 mg/kg, about 175 mg/kg, about 180 mg/kg, about 190 mg/kg, about 200 mg/kg, or more. In some embodiments, the riluzole is administered twice per day, daily, every 48 hours, every 72 hours, twice per week, once per week, once every two weeks, once per month, once every 2 months, once every 3 months, or once every 6 months. In some embodiments, the dose of riluzole is dependent upon the subject's weight and/or age.

In some embodiments, mecasermin is administered separately, simultaneously, or sequentially with the mitochondria-targeting peptidomimetic(s). In some embodiments, the dose of mecasermin is about 0.5 mg/kg to about 2 mg/kg, about 1 mg/kg to about 2 mg/kg, about 0.5 mg/kg to about 5 mg/kg, about 5 mg/kg to about 100 mg/kg, about 10 mg/kg to about 75 mg/kg, or about 25 mg/kg to about 50 mg/kg. In some embodiments, the dose of resveratrol is 0.8 mg/kg, about 5 mg/kg, about 10 mg/kg, about 20 mg/kg, about 25 mg/kg, about 30 mg/kg, about 40 mg/kg, about 50 mg/kg, about 60 mg/kg, about 75 mg/kg, about 80 mg/kg, about 90 mg/kg, about 100 mg/kg, about 110 mg/kg, about 120 mg/kg, about 125 mg/kg, about 130 mg/kg, about 140 mg/kg, about 150 mg/kg, about 160 mg/kg, about 175 mg/kg, about 180 mg/kg, about 190 mg/kg, about 200 mg/kg, or more. In some embodiments, the mecasermin is administered twice per day, daily, every 48 hours, every 72 hours, twice per week, once per week, once every two weeks, once per month, once every 2 months, once every 3 months, or once every 6 months. In some embodiments, the dose of mecasermin is dependent upon the subject's weight and/or age.

In one embodiment, an additional therapeutic agent is administered to a subject in combination with at least one mitochondria-targeting peptidomimetic, such that a synergistic therapeutic effect is produced. For example, administration of at least one mitochondria-targeting peptidomimetic with one or more additional therapeutic agents for the prevention or treatment of ALS will have greater than additive effects in the prevention or treatment of the disease. Therefore, lower doses of one or more of any individual therapeutic agent may be used in treating or preventing ALS resulting in increased therapeutic efficacy and decreased side-effects. In some embodiments, at least one mitochondria-targeting peptidomimetic is administered in combination with one or more a riluzole (Rilutek®), edaravone (Radicava®), mecasermin, baclofen (Lioresal®), diazepam (Valium®), dantrolene (Dantrium®), nonsteroidal anti-inflammatory agents, anticonvulsive medications (e.g., carbamazepine (Tegretol) or phenytoin (Dilantin®)), amitriptyline (Elavil®), nortriptyline (Pamelor™), or Lorazepam (Ativan®), such that a synergistic effect in the prevention or treatment of ALS results. In some embodiments, the additional therapeutic agent is elamipretide (also known as SS-31 or bendavia).

In some embodiments, the mitochondria-targeting peptidomimetics, such as (R)-2-amino-N—((S)-1-(((S)-5-amino-1-(3-benzyl-1,2,4-oxadiazol-5-yl)pentyl)amino)-3-

(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt) may be combined with one or more additional therapies for the prevention or treatment of α-synucleinopathies. In some embodiments of the methods of the present technology, the mitochondria-targeting peptidomimetic is (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (e.g., (Ia)). In some embodiments, additional therapies include, but are not limited to, administration of levodopa. In one embodiment, an additional therapeutic agent is administered to a subject in combination with at least one mitochondria-targeting peptidomimetic, such that a synergistic therapeutic effect is produced. For example, administration of at least one mitochondria-targeting peptidomimetic with one or more additional therapeutic agents for the prevention or treatment of α-synucleinopathies will have greater than additive effects in the prevention or treatment of the disease. Therefore, lower doses of one or more of any individual therapeutic agent may be used in treating or preventing α-synucleinopathies resulting in increased therapeutic efficacy and decreased side-effects.

In some embodiments, the mitochondria-targeting peptidomimetics, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), a monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a trihydrochloride salt (e.g., (Ia)), a mono-tosylate salt, a bis-tosylate salt, or a tri-tosylate salt) may be combined with one or more additional therapies for the prevention or treatment of TDP-43 proteinopathies. In some embodiments of the methods of the present technology, the mitochondria-targeting peptidomimetic is (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt thereof (e.g., (Ia)). In some embodiments, additional therapies include, but are not limited to, administration of antidepressants, such as SSRI antidepressants including trazodone. In one embodiment, an additional therapeutic agent is administered to a subject in combination with at least one mitochondria-targeting peptidomimetic, such that a synergistic therapeutic effect is produced. For example, administration of at least one mitochondria-targeting peptidomimetic with one or more additional therapeutic agents for the prevention or treatment of TDP-43 proteinopathies will have greater than additive effects in the prevention or treatment of the disease. Therefore, lower doses of one or more of any individual therapeutic agent may be used in treating or preventing TDP-43 proteinopathies resulting in increased therapeutic efficacy and decreased side-effects.

In some embodiments, multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

EXAMPLES

The present technology is further illustrated by the following examples, which should not be construed as limiting in any way.

Example 1—Use of Mitochondria-Targeting Peptidomimetic Compounds in the Treatment of ALS in an Animal Model This example demonstrates the use of mitochondria-targeting peptidomimetic compounds, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri-(tris-) acid salt), monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a tri-hydrochloride salt (i.e., (Ia)), a mono-tosylate salt, a bis-tosylate salt, or a tri-tosylate salt), stereoisomer, tautomer, hydrate, and/or solvate thereof in the treatment of ALS in an animal model of the disease.

Methods

Study Design. Three experimental groups of n=20 (10 male, 10 female) SOD1 G93A high copy transgenic mice were dosed daily via intraperitoneal administration of vehicle control; (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (as its tris-HCl salt—(Ia)) at 0.5 mg/kg; or (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (as its tris-HCl salt—(Ia)) at 5.0 mg/kg. Animals were dosed beginning at 8 weeks of age and dosing was continued until humane end of life (defined by the inability of animal to right itself from either side within 30 seconds when placed on its side). Experimental endpoints and in-life collections and observations were as follows:

1. Bodyweight measurement. Daily recording of weight.
2. Neurological scoring. Weekly NeuroScore, a qualitative assessment of neurological disease progression based upon a five-point grading system. Scoring is defined as follows:
   Score 0: Full extension of hind legs away from the lateral midline when the mouse is suspended by its tail, and the mouse can hold this extension for 2 seconds, being suspended 3 times consecutively.

Score 1: Collapse or partial collapse of the leg extension toward the lateral midline or trembling of hind legs during the tail suspension.

Score 2: Toes curl under at least twice during walking of 12 inches, or any part of the foot is dragging along the cage bottom or table.

Score 3: Rigid paralysis or minimal joint movement, the foot is not being used for forward motion.

Score 4: The mouse cannot right itself within 30 sec from either side.

3. Grip strength test. Weekly forelimb grip strength, performed as follows:
   a. Subjects are weighed and acclimated to the testing room for at least 60 min.
   b. Equipment: Bioseb grip strength meter equipped with a grid for grasping that is suited for mice.
   c. Mice are lowered towards the grid by their tails to allow for visual placing and for the mouse to grip the grid with their forepaws.
   d. Subjects are firmly pulled horizontally away from the grid (parallel to the bench) for 3 consecutive trials with a brief (approximately 30 sec) rest period on the bench between trials.
   e. The average force in grams of the 3 forepaw and 3 all-paws trials are analyzed with and without normalization to body weight.

4. Retro-orbital blood collection. Bi-weekly retroorbital eye bleeds to determine drug exposure levels as well as levels of neurofilament light chain, a biomarker of axonal damage shown to correlate with ALS disease progression in human patients. Briefly, mice are sedated with isoflurane (5% induction, 2% maintenance) in $O_2$. When they reach the plane of anesthesia, mice are withdrawn from isoflurane and blood is collected with a 25 μL glass capillary tube from the retro-orbital sinus, alternating sides for successive bleeds. 200 μL of whole blood is collected in a BD $K_2$EDTA Microtainer collection tube containing 3.5 μL of 25×HALT protease inhibitor cocktail and kept on ice for processing. Mice are allowed to recover from the anesthesia, then returned to their home cage.

Results

Figure 1B:
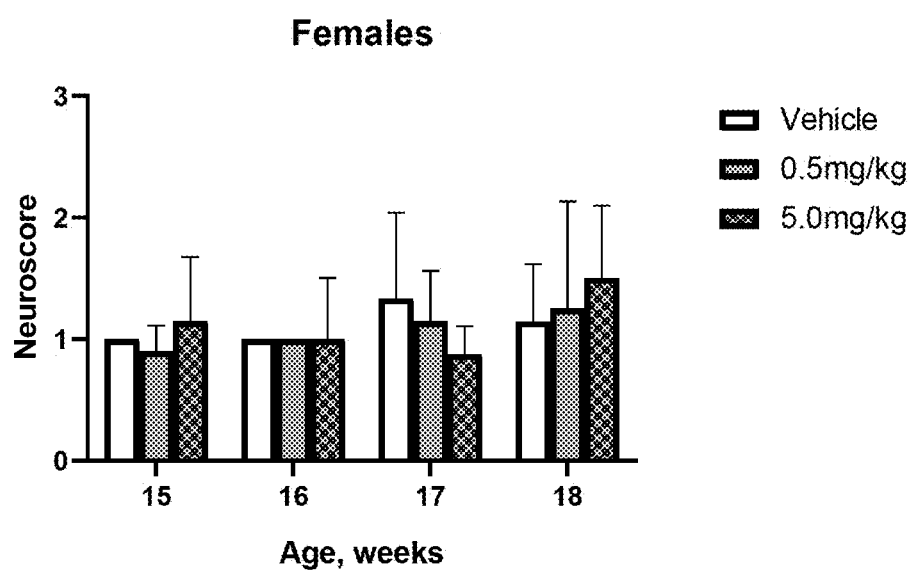

Systemic administration of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide delays neurological symptom progression in ALS. As described above, mice were treated daily with intraperitoneal injections of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (Ia) or vehicle control from 8 weeks of age until humane end of life. Progression of neurological disease was measured weekly using a five-point neurological scoring ratings scale (please refer to study design for scoring metrics shown above). (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (as its tris-HCl salt (Ia)) at a dose of 5.0 mg/kg delayed the progression of neurological symptom onset in male animals relative to vehicle treated animals, as determined by two-way ANOVA (FIG. 1A). There were no effects in female mice, which present with a milder phenotype in this transgenic model (FIG. 1B).

Figure 1C:
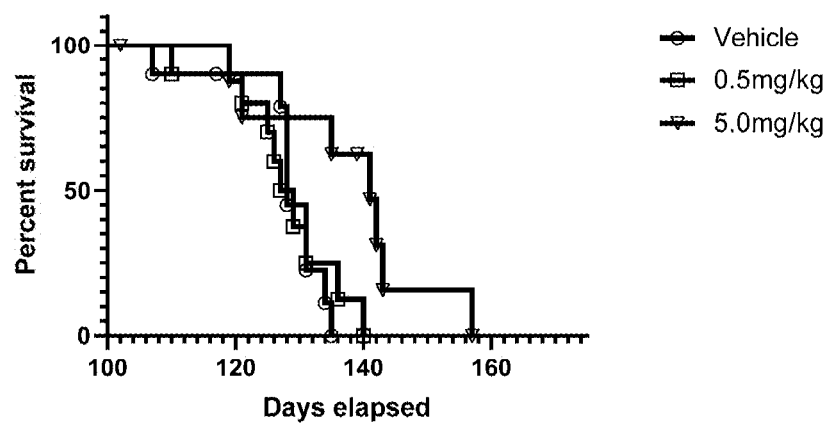
Figure 1D:
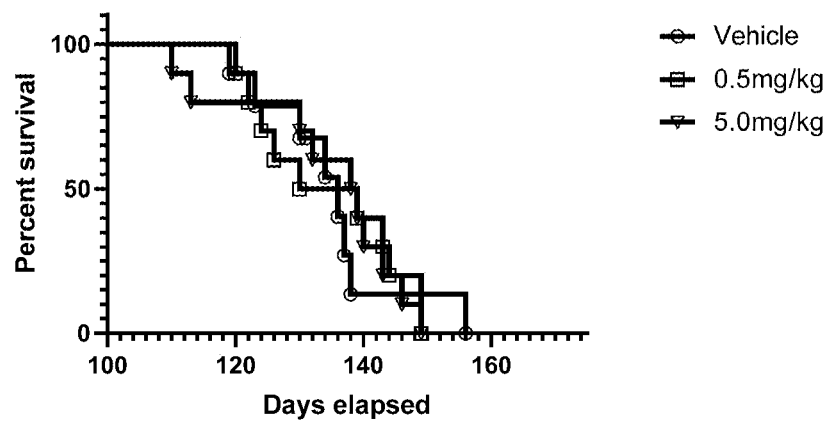

Systemic administration of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide prolongs lifespan in ALS mouse model. The lifespan of male animals dosed with (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide at 5.0 mg/kg was significantly increased compared to vehicle control (FIG. 1C). There were no effects in female mice, which present with a milder disease phenotype in this transgenic model (FIG. 1D).

Figure 2A:
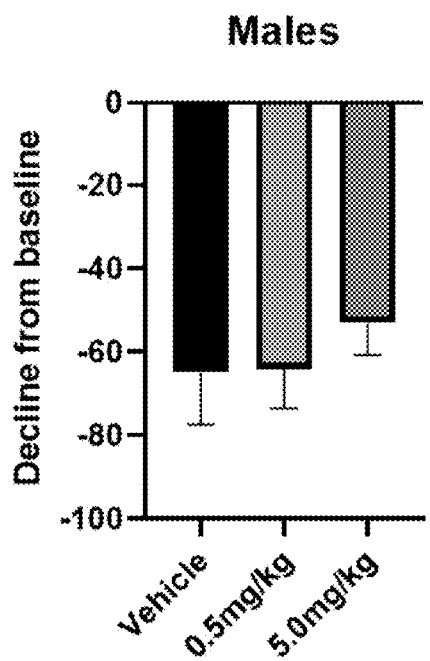
FIGS. 2A-2B: Systemic administration of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide.3HC (Ia) attenuates the loss of grip strength in male SOD1 G93A transgenic mice.
Figure 2B:
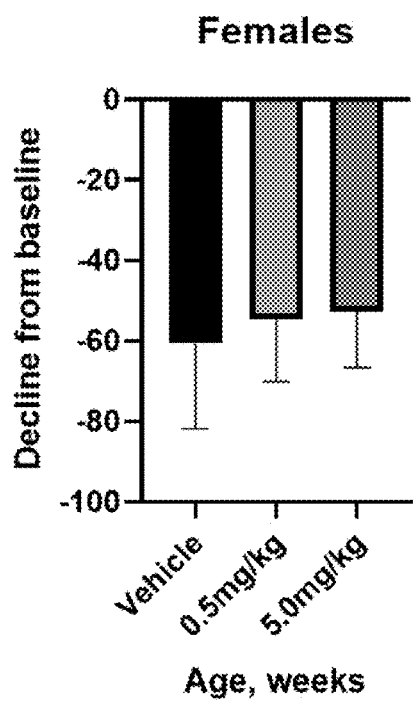

Systemic administration of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide attenuates decline in muscle strength in ALS mouse model. As shown in FIG. 2A and Table 1A, systemic administration of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (as its tris-HCl salt—(Ia)) attenuates the loss of grip strength in male SOD1 G93A transgenic mice. Grip strength values were determined at baseline (week 8) and through end of life for each animal. The mean of individual animal decline is depicted for animals following 10 weeks on drug. Male animals treated with high dose (5.0 mg/kg) (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (as its tris-HCl salt—(Ia)) demonstrated a trend in protection from loss of grip strength, although the magnitude of effect falls just short of statistical significance (p=0.08).

TABLE 1A

Statistical analysis of grip strength in male SOD1 G93A transgenic mice.

| Dunnett's multiple comparisons test | Mean Diff. | 95.00% CI of diff. | Significant? | Summary | Adjusted P Value |
|---|---|---|---|---|---|
| Vehicle vs. 0.5 mg/kg | −0.7940 | −14/23 to 12/64 | No | ns | 0.9857 |
| Vehicle vs. 5.0 mg/kg | −11.90 | −25.33 to 1.539 | No | ns | 0.0855 |

TABLE 1B

Statistical analysis of grip strength in female SOD1 G93A transgenic mice.

| Dunnett's multiple comparisons test | Mean Diff. | 95.00% CI of diff. | Significant? | Summary | Adjusted P Value |
|---|---|---|---|---|---|
| Vehicle vs. 0.5 mg/kg | −6.081 | −28.93 to 16.77 | No | ns | 0.7518 |
| Vehicle vs. 5.0 mg/kg | −7.905 | −29.16 to 13.35 | No | ns | 0.5847 |

Figure 3A:
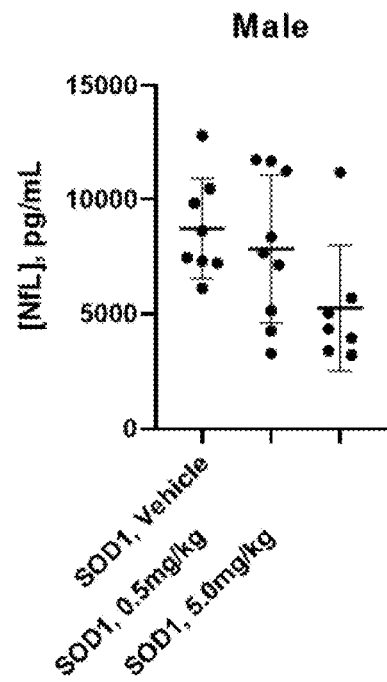
FIGS. 3A-3B: Systemic administration of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide-3HCl (Ia) decreases accumulation of neurofilament light chain (NfL) in the plasma of male SOD1 G93A transgenic mice.
Figure 3B:
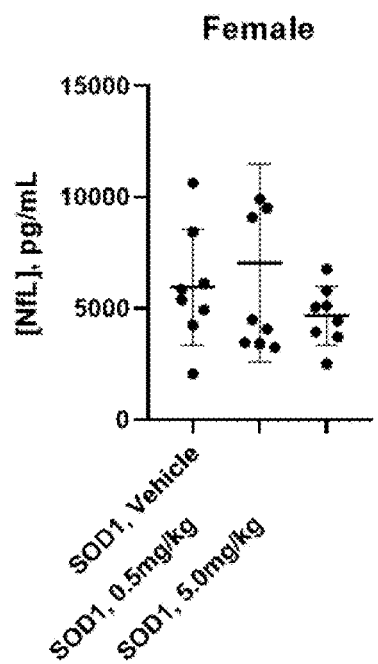

Systemic administration of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide decreases plasma accumulation of neurofilament light chain (NfL) in ALS mouse model. Systemic administration of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide decreases accumulation of neurofilament light chain (NfL) in the plasma of male SOD1 G93A transgenic mice. Shown in FIGS. 3A-3B (and Tables 2A-2B) are plasma levels of NfL, a marker of axonal damage, following 10 weeks of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide or vehicle control administration. (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (as its tris-HCl salt—(Ia)) at 5.0 mg/kg had a statistically significant impact on the accumulation of NfL in male transgenic mice, suggesting protection from axonal damage in the CNS (FIG. 3A). Note that female mice had lower overall levels of NfL, consistent with the milder disease phenotype associated with female mice in this model (FIG. 3B).

TABLE 2A

Statistical analysis of plasma NfL levels in male SOD1 G93A transgenic mice.

| Dunnett's multiple comparisons test | Mean Diff. | 95.00% CI of diff. | Significant? | Summary | Adjusted P Value |
|---|---|---|---|---|---|
| Vehicle vs. 0.5 mg/kg | 897.8 | −2295 to 4091 | No | ns | 0.7331 |
| Vehicle vs. 5.0 mg/kg | 3469 | 68.21 to 6870 | Yes | * | 0.0453 |

TABLE 2B

Statistical analysis of plasma NfL levels in female SOD1 G93A transgenic mice.

| Dunnett's multiple comparisons test | Mean Diff. | 95.00% CI of diff. | Significant? | Summary | Adjusted P Value |
|---|---|---|---|---|---|
| Vehicle vs. 0.5 mg/kg | −1075 | −4678 to 2529 | No | ns | 0.7058 |
| Vehicle vs. 5.0 mg/kg | 1291 | −2417 to 4999 | No | ns | 0.6270 |

Figure 4:
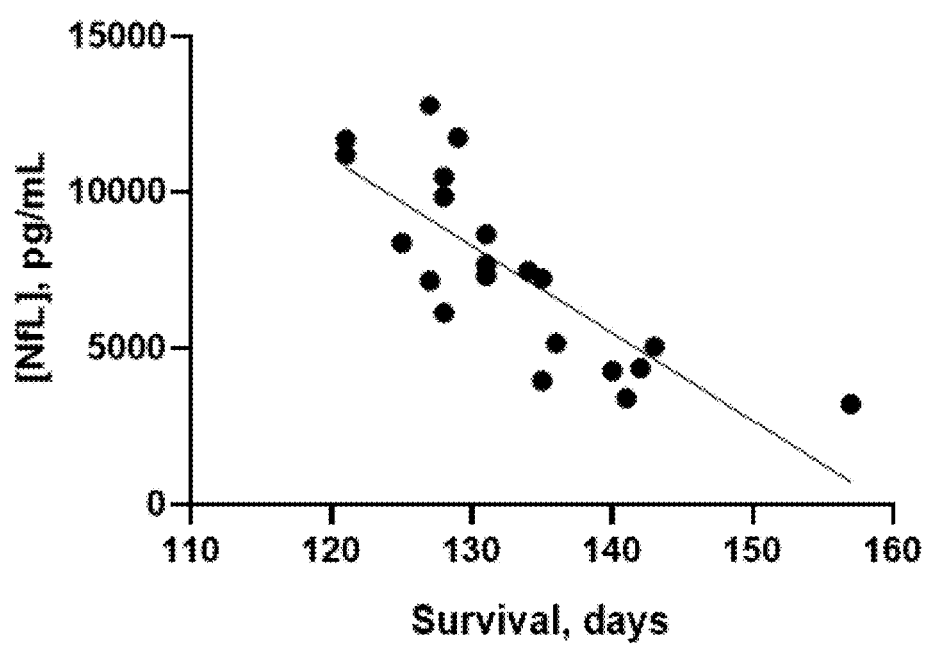
FIG. 4 is a chart showing the correlation between plasma neurofilament levels and animal survival in male SOD1 G93A transgenic mice. Depicted are plasma NfL levels for every male mouse in this study plotted as a function of their age at humane end of life.

As shown in FIG. 4 (and Table 3), there is a significant correlation between plasma neurofilament levels and animal survival in male SOD1 G93A transgenic mice. Depicted are plasma NfL levels for every male mouse in this study plotted as a function of their age at humane end of life. The correlation between accumulation of the axonal damage biomarker and animal lifespan is highly significant, suggesting that (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (Ia) prolongs the lifespan of male SOD1 G93A mice at least partly through protection of axonal loss or damage in the CNS.

TABLE 3

Statistical analysis of correlation between plasma neurofilament levels and animal survival in male SOD1 G93A transgenic mice.

| Pearson r | |
|---|---|
| r | −0.7953 |
| 95% confidence interval | −0.9134 to −0.5538 |
| R squared | 0.6325 |
| P value | |
| P (two-tailed) | <0.0001 |
| P value summary | **** |
| Significant? (alpha = 0.05) | Yes |
| Number of XY Pairs | 21 |

These results demonstrate that mitochondria-targeting peptidomimetic compounds, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri-(tris-) acid salt), monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a tri-hydrochloride salt (i.e., (Ia)), a mono-tosylate salt, a bis-tosylate salt, or a tri-tosylate salt), stereoisomer, tautomer, hydrate, and/or solvate thereof are useful in the treatment of ALS as they are useful in ameliorating one or more of the following symptoms: delays onset of neurological symptoms of ALS, increases survival, attenuates decline in muscle strength, and/or decreases plasma neurofilament light chain (NfL) levels. Accordingly, (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide is useful in methods to treat subjects in need thereof for the treatment of ALS.

Example 2—Use of Mitochondria-Targeting Peptidomimetic Compounds in the Treatment of ALS This example prophetically demonstrates the use of mitochondria-targeting peptidomimetic compounds, such as (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a tri-hydrochloride salt (i.e., (Ia)), a mono-tosylate salt, a bis-tosylate salt, or a tri-tosylate salt), stereoisomer, tautomer, hydrate, and/or solvate thereof in the treatment of ALS in a subject in need thereof.

Methods

Subjects suspected of having or diagnosed as having ALS receive daily administrations of 1 mg/kg body weight of (R)-2-amino-N—((S)-1-(((S)-5-amino-1-(3-benzyl-1,2,4- oxadiazol-5-yl)pentyl)amino)-3-(4-hydroxy-2,6-dimethylphenyl)-1-oxopropan-2-yl)-5-guanidinopentanamide (I), or a pharmaceutically acceptable salt (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri-(tris-) acid salt), monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a tri-hydrochloride salt (i.e., (Ia)), a mono-tosylate salt, a bis-tosylate salt, or a tri-tosylate salt), stereoisomer, tautomer, hydrate, and/or solvate thereof alone or in combination with one or more additional therapeutic agents for the treatment or prevention of ALS. Peptidomimetics and/or additional therapeutic agents are administered orally, topically, systemically, intravenously, subcutaneously, intravitreally, intraperitoneally, or intramuscularly according to methods known in the art. Subjects will be evaluated weekly for the presence and/or severity of signs and symptoms associated with ALS including, but not limited to, e.g., muscle weakness, muscle wasting (atrophy), muscle fasciculations, muscle spasticity, slowness of movement, poor balance, incoordination, alterations in vocal quality, dysarthria, dysphagia, incomplete eye closure, drooling, pseudobulbar affect, premature death, increased brain translocator protein-18 kDa (TSPO) expression, and plasma accumulation of neurofilament light chain (NfL). Treatments are maintained until such a time as one or more signs or symptoms of ALS are ameliorated or eliminated.

Results

It is predicted that subjects suspected of having or diagnosed as having ALS and receiving therapeutically effective amounts of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a tri-hydrochloride salt (i.e., (Ia)), a mono-tosylate salt, a bis-tosylate salt, or a tri-tosylate salt), stereoisomer, tautomer, hydrate, and/or solvate thereof will display reduced severity or elimination of one or more symptoms associated with ALS. It is further expected that administration of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I) in combination with one or more additional therapeutic agents will have synergistic effects in this regard compared to that observed in subjects treated with the mitochondria-targeting peptidomimetic compound or the additional therapeutic agents alone.

These results will show that (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a tri-hydrochloride salt (i.e., (Ia)), a mono-tosylate salt, a bis-tosylate salt, or a tri-tosylate salt), stereoisomer, tautomer, hydrate, and/or solvate thereof is useful in the treatment of ALS. These results will show that (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (I), or a pharmaceutically acceptable salt (such as a tartrate salt, a fumarate salt, a citrate salt, a benzoate salt, a succinate salt, a suberate salt, a lactate salt, an oxalate salt, a phthalate salt, a methanesulfonate salt, a benzenesulfonate salt or a maleate salt (in each case a mono-, bis- or tri- (tris-) acid salt), monoacetate salt, a bis-acetate salt, a tri-acetate salt, a mono-trifluoroacetate salt, a bis-trifluoroacetate salt, a tri-trifluoroacetate salt, a monohydrochloride salt, a bis-hydrochloride salt, a tri-hydrochloride salt (i.e., (Ia)), a mono-tosylate salt, a bis-tosylate salt, or a tri-tosylate salt), stereoisomer, tautomer, hydrate, and/or solvate thereof is useful in ameliorating one or more of the following symptoms: muscle weakness, muscle wasting (atrophy), muscle fasciculations, muscle spasticity, slowness of movement, poor balance, incoordination, alterations in vocal quality, dysarthria, dysphagia, incomplete eye closure, drooling, pseudobulbar affect, premature death, increased brain translocator protein-18 kDa (TSPO) expression, and plasma accumulation of neurofilament light chain (NfL). Accordingly, the peptidomimetics are useful in methods to treat subjects in need thereof for the treatment of ALS.

Example 3—Mitochondria-Targeting Peptidomimetic Compounds of the Present Technology Exhibit Higher Brain Exposure as Compared to Elamipretide & Demonstrate Mitochondrial Protective Effects This example compares, in a rat model, (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (Ia), and elamipretide with respect to brain uptake and Compound Ia's pharmacological effect on reducing mitochondrial reactive oxygen species (ROS) and preserving ATP production under conditions of oxidative stress.

Methods

Figure 5A:
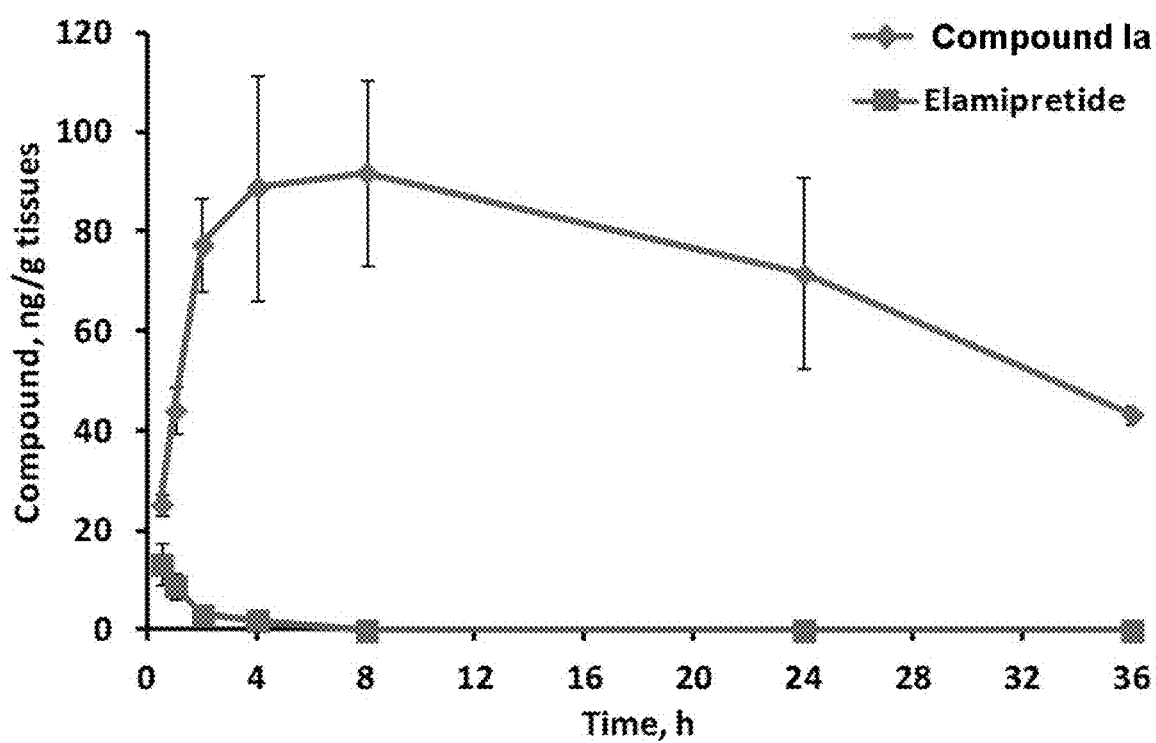
FIG. 5A is a graph comparing accumulation of drug in the brain of Sprague Dawley rats over 36 hours where the rats are subcutaneously injected with (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide.3HCl (Ia) or elamipretide; both administered at 5 mg/kg. n=4 per time-point.

Sprague Dawley rats were injected subcutaneously with 5 mg/kg of Compound Ia or elamipretide (n=4 per time-point). Animals were sacrificed at the indicated timepoints and transcardial perfusion was performed. Drug levels in whole brain homogenate were determined by LC-MS/MS. Results are presented in FIG. 5A.

Ischemic stroke was induced in Sprague Dawley rats via middle cerebral artery occlusion with the vasoconstrictive peptide endothelin-1 (ET-1; 240 pmol per injection). Compound Ia was administered to each rat at 24 and 4 hours prior to onset of ischemia via subcutaneous injection at 5 mg/kg. Mitochondrial respiration was measured in brain homogenate excised from the infarcted area 24 hours following the onset of ischemia using high resolution respirometry (OxyGraph O2K). Respiratory control ratio was calculated as complex I supported oxidative phosphorylation divided by Complex I linked leak respiration. Results are illustrated in FIG. 5B, ** $p<0.01$, one-way ANOVA.

Results

Figure 5B:
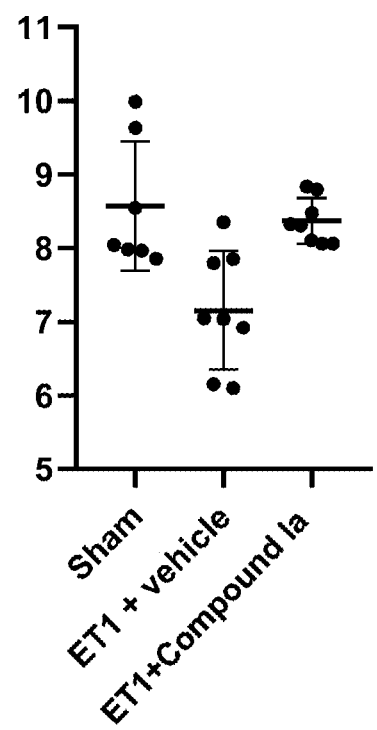
FIG. 5B is a graph comparing the respiratory control ratio of mitochondrial respiration in brain homogenate prepared from Sprague Dawley rats that were treated with (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide-3HCl (Ia) at 5 mg/kg as compared with an untreated group and a Sham group. ** p<0.01, one way ANOVA.

Brain exposure of Compound Ia was higher than that of elamipretide (FIG. 5A), and Compound Ia restored mitochondrial respiration in brain under conditions of oxidative stress (FIG. 5B). These findings demonstrate that Compound Ia is suitable for the treatment of neurodegenerative diseases where mitochondrial damage in the central nervous system contributes to pathomechanism.

Example 4—Mitochondria-Targeting Peptidomimetic Compounds Attenuate Dopaminergic Neuron Loss in the Substantia Nigra of Mutant Alpha-Synuclein Transduced Mice This example demonstrates the use of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (Ia) in a mouse model of mutant alpha-synuclein-induced dopaminergic neuron loss as a means to examine possible drug efficacy in a model of neurodegenerative disease.

Methods

Dopaminergic neuron loss in the substantia nigra pars compacta (SNc) was induced in wildtype C57BL/6 mice using AAV9 mediated viral delivery of human alpha-synuclein harboring the pathogenic A53T mutation. $4 \times 10^{10}$ viral particles per SNc were injected bilaterally via stereotactic surgery. Animals were nine weeks of age when viral transduction was performed. Animals were treated daily with intraperitoneal administration of (Ia) beginning 24 hours before viral transduction and continued for 5 weeks. Experimental groups were as follows:

1. Group A—AAV A53T injected, vehicle treatment (n=7)
2. Group B1—AAV A53T injected, (Ia) at 0.5 mg/kg treatment (n=8)
3. Group B2—AAV A53T injected, (Ia) at 5.0 mg/kg treatment (n=8)
4. Group C1—Sham AAV9 injected, (Ia) at 0.5 mg/kg treatment (n=6)
5. Group C2—Sham AAV9 injected, (Ia) at 5.0 mg/kg treatment (n=7)

Figure 6A:
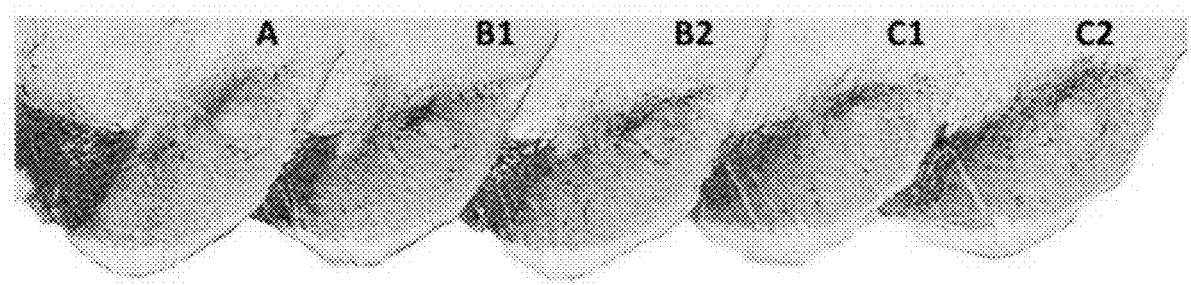
FIG. 6A is an image of immunostained dopaminergic neurons of C57BL/6 mice injected with A53T mutant alpha-synuclein viral particles and then treated with either 0.5 mg/kg or 5 mg/kg of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide.3HCl (Ia) as compared with an untreated group and a group where no A53T mutant alpha-synuclein vial particles were injected into the animal. A=A53T AAV, no drug; B1=A53T AAV, Compound Ia 0.5 mg/kg; B2=A53T AAV, Compound Ia 5.0 mg/kg; C1=No virus, Compound Ia 0.5 mg/kg; C2=No virus, Compound Ia 5.0 mg/kg.
Figure 6B:
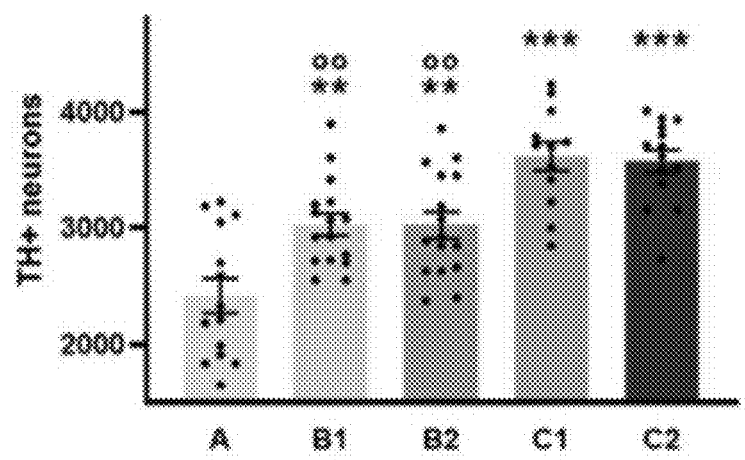
FIG. 6B is a bar graph representation of the data obtained from the experiment referred to in FIG. 6A. A=A53T AAV, no drug; B1=A53T AAV, Compound Ia 0.5 mg/kg; B2=A53T AAV, Compound Ia 5.0 mg/kg; C1=No virus, Compound Ia 0.5 mg/kg; C2=No virus, Compound Ia 5.0 mg/kg.  p<0.01 vs group A; * p<0.001 vs group A; $^{OO}$ p<0.001 vs group C1 and C2.

Five weeks following viral transduction, animals were sacrificed and brains were removed and processed for immunohistochemistry and cell counts (i.e., number of TH positive neurons) in the substantia nigra pars compacta were performed via automated stereology. Serial sections were cut and stained with tyrosine hydroxylase (TH) to enumerate the number of dopaminergic neurons. Results are illustrated in FIGS. 6A and 6B; ** $p<0.01$ vs groups;* $p<0.001$ vs group A; $^{OO}$ $p<0.001$ vs group C1 and C2.

Figure 6C:
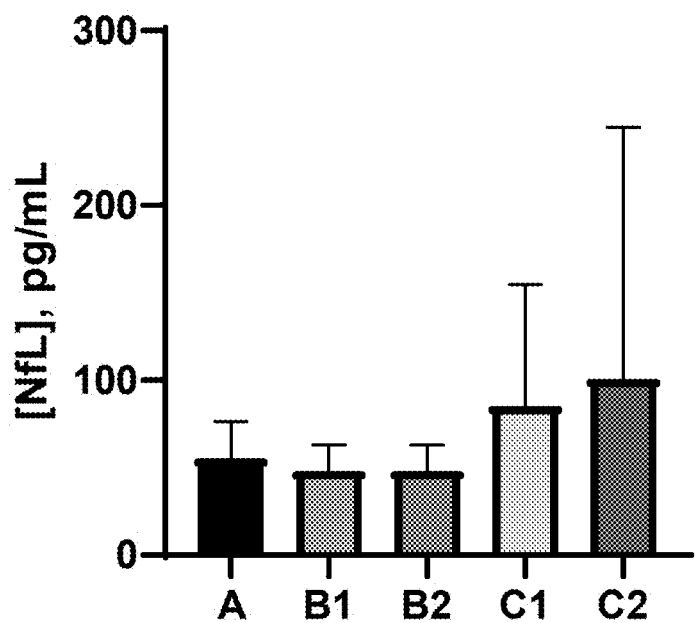
FIG. 6C is bar graph of data for plasma neurofilament analysis of C57BL/6 mice following injection with A53T mutant alpha-synuclein viral particles for each of the animal groups represented in FIGS. 6A and 6B. A=A53T AAV, no drug; B1=A53T AAV, Compound Ia 0.5 mg/kg; B2=A53T AAV, Compound Ia 5.0 mg/kg; C1=No virus, Compound Ia 0.5 mg/kg; C2=No virus, Compound Ia 5.0 mg/kg.

Plasma neurofilament light chain levels were determined by SIMOA assay from blood collected at sacrifice and the results are presented in FIG. 6C. No statistical significance is seen between groups by one-way ANOVA.

Results

Mutant alpha-synuclein-induced loss of dopaminergic neurons in the substantia nigra was significantly attenuated by Compound Ia, FIGS. 6A and 6B. Neurofilament levels were not elevated by this induction protocol (FIG. 6C). Therefore, treatment with Compound Ia prevented the loss of dopaminergic neurons in the substantia nigra following mutant alpha-synuclein toxicity. Accordingly, these data demonstrate that Compound Ia may be useful in methods for the treatment or prevention of neurodegenerative disease caused by alpha-synucleinopathy, such as Parkinson's Disease (PD), PD with dementia, dementia with Lewy bodies, and Multiple System Atrophy.

Example 5—Mitochondria-Targeting Peptidomimetic Compounds are Neuroprotective in Primary Mutant TDP43 Expressing Upper Motor Neurons This example examines the neuroprotective effect of (R)-2-amino-N—((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide (Ia) in primary cells derived from the prp-TDP-43$^{A315T}$-UeGFP mouse model.

Methods

Figure 7:
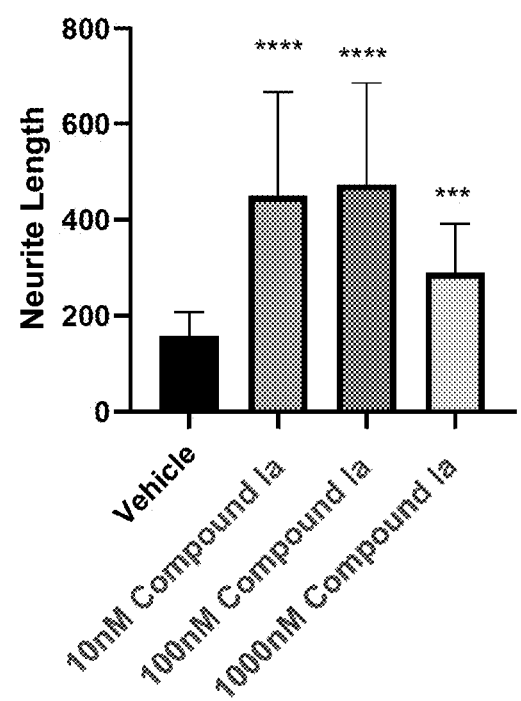
FIG. 7 is a bar graph of data for average neurite length per cell for a study of the effect of Compound Ia at various concentrations on corticospinal motor neurons derived from a prp-TDP-43$^{A315T}$-UeGFP mouse model. * p<0.001 vs vehicle; ** p<0.0001 vs vehicle.

Studies were performed in primary cells derived from the prp-TDP-43$^{A315T}$-UeGFP mouse model (Gautam, et al. Acta Neuropathol. 2019 January; 137(1): 47-69). Briefly, these mice express a pathogenic human TDP43 transgene which leads to severe structural alterations in the mitochondria, nucleus, and endoplasmic reticulum on the background of an eGFP reporter mouse. Both transgene (prp) and reporter (UCHL1) are driven by tissue specific promoter elements, leading to the generation of fluorescent green corticospinal motor neurons carrying the TDP43 mutation. Utilizing the endogenous fluorescence of the eGFP reporter, corticospinal motor neurons can be directly visualized in situ. Mixed cortical cultures were derived from the brains of prp-TDP-43$^{A315T}$-UeGFP mice and allowed to divide in serum free minimal medium for 3 cell divisions. Culture media+/−drug was removed and replenished daily. Doses of Compound Ia utilized in the experiment were 10 nM; 100 nM and 1000 nM. Drug was prepared in DMSO vehicle, and DMSO was used as vehicle control (<1% volume/volume). Cells were imaged using standard fluorescent microscopy techniques. Neurite length was calculated using automated imaging software (NIH Image J) on GFP expressing cells. Three independent biological replicates were performed, with a minimum of 10 motor neurons imaged per each replicate. Average neurite length per cell is presented in FIG. 7. Statistical analysis was performed by one-way ANOVA using Dunnett's multiple comparisons test. * $p<0.001$ vs vehicle; ** $p<0.0001$ vs vehicle.

Results

Treatment with Compound Ia improved neurite length at all doses assessed in primary upper motor neuron cultures derived from A315T mutant TDP43 transgenic mice. Accordingly, these data demonstrate that Compound Ia may be efficacious in methods for treating or preventing diseases of TDP-43 proteinopathy, including ALS and Frontotemporal Lobar Degeneration (FTLD).

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a nonlimiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for treating or inhibiting α-synucleinopathy or TAR DNA binding protein 43 (TDP-43) proteinopathy in a subject in need thereof, comprising administering to the subject a therapeutically effective amount of the peptidomimetic (R)-2-amino-N-((S)-1-(((S)-5-amino-1-(3-benzyl-1,2,4-oxadiazol-5-yl)pentyl)amino)-3-(4-hydroxy-2,6-dimethylphenyl)-1-oxopropan-2-yl)-5-guanidinopentanamide, or a pharmaceutically acceptable salt, stereoisomer, tautomer, hydrate, and/or solvate thereof.

2. The method of claim 1, wherein the subject has been diagnosed as having an α-synucleinopathy or a TDP-43 proteinopathy.

3. The method of claim 2, wherein the a-synucleinopathy is Parkinson's Disease (PD), PD with dementia, dementia with Lewy bodies, or Multiple System Atrophy (MSA).

4. The method of claim 2, wherein the TDP-43 proteinopathy is amyotrophic lateral sclerosis (ALS) or Frontotemporal Lobar Degeneration (FTLD).

5. The method of claim 1, wherein the peptidomimetic is administered daily for 2 weeks or more.

6. The method of claim 1, wherein the peptidomimetic is administered daily for 12 weeks or more.

7. The method of claim 1, wherein the treating or inhibiting of α-synucleinopathy comprises attenuating the loss of dopaminergic neurons in the subject as compared to untreated controls.

8. The method of claim 1, wherein the treating or inhibiting of TDP-43 proteinopathy comprises an increase in neurite length in the subject as compared to untreated controls.

9. The method of claim 1, wherein the subject is a mammal.

10. The method of claim 9, wherein the mammalian subject is a human.

11. The method of claim 1, wherein the peptidomimetic is administered orally or subcutaneously.

12. The method of claim 1, wherein the peptidomimetic is administered topically, intranasally, systemically, intravenously, intraperitoneally, intradermally, intraocularly, ophthalmically, intrathecally, intracerebroventricularly, iontophoretically, transmucosally, intravitreally, or intramuscularly.

13. The method of claim 1, further comprising separately, sequentially, or simultaneously administering an additional treatment to the subject.

14. The method of claim 13, wherein the additional treatment comprises administration of a therapeutic agent.

15. The method of claim 14, wherein the therapeutic agent comprises levodopa for the treatment of α-synucleinopathy, and wherein the therapeutic agent comprises a selective serotonin reuptake inhibitor (SSRI) antidepressant for the treatment of TDP-43 proteinopathy.

16. The method of claim 13, wherein the combination of peptidomimetic and an additional therapeutic treatment has a synergistic effect in the prevention or treatment of α-synucleinopathy or TDP-43 proteinopathy.

17. The method of claim 1, wherein the pharmaceutically acceptable salt comprises a tartrate salt, a fumarate salt, monoacetate salt, a bis-acetate salt, a tri-acetate salt, a mono-trifluoroacetate salt, a bis-trifluoroacetate salt, a trifluoroacetate salt, a monohydrochloride salt, a bis-hydrochloride salt, a trihydrochloride salt, a mono-tosylate salt, a bis-tosylate salt, or a tri-tosylate salt.

18. The method of claim 1, wherein the peptidomimetic is formulated as a tris-HCl salt, a bis-HCl salt, or a mono-HCl salt.

* * * * *